US011999985B2

United States Patent
Singh et al.

(10) Patent No.: US 11,999,985 B2
(45) Date of Patent: *Jun. 4, 2024

(54) CELLULOSIC ENZYME RECYCLING FROM SEPARATION OF SACCHARIFIED BIOMASS

(71) Applicant: Edeniq, Inc., Visalia, CA (US)

(72) Inventors: Deepak Singh, Fresno, CA (US); Sandra Jacobson, El Cajon, CA (US); Kris Ramos, Sanger, CA (US); Prachand Shrestha, Visalia, CA (US)

(73) Assignee: Edeniq Inc., Visalia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/957,633

(22) Filed: Sep. 30, 2022

(65) Prior Publication Data

US 2023/0104032 A1  Apr. 6, 2023

Related U.S. Application Data

(60) Continuation of application No. 16/360,408, filed on Mar. 21, 2019, now Pat. No. 11,492,649, which is a division of application No. 14/775,588, filed as application No. PCT/US2014/029032 on Mar. 14, 2014, now Pat. No. 10,260,081.

(60) Provisional application No. 61/798,070, filed on Mar. 15, 2013.

(51) Int. Cl.
| | |
|---|---|
| *C12P 19/14* | (2006.01) |
| *C07H 3/04* | (2006.01) |
| *C12P 7/10* | (2006.01) |
| *C12P 19/02* | (2006.01) |
| *C12P 19/12* | (2006.01) |
| *C13K 1/02* | (2006.01) |
| *C13K 13/00* | (2006.01) |

(52) U.S. Cl.
CPC ............... *C12P 19/14* (2013.01); *C07H 3/04* (2013.01); *C12P 7/10* (2013.01); *C12P 19/02* (2013.01); *C12P 19/12* (2013.01); *C13K 1/02* (2013.01); *C13K 13/002* (2013.01); *C12P 2201/00* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 4,867,876 A | 9/1989 | Kopf | |
| 4,882,050 A | 11/1989 | Kopf | |
| 5,034,124 A | 7/1991 | Kopf | |
| 5,049,268 A | 9/1991 | Kopf | |
| 5,232,589 A | 8/1993 | Kopf | |
| 5,342,517 A | 8/1994 | Kopf | |
| 5,593,580 A | 1/1997 | Kopf | |
| 5,868,930 A | 2/1999 | Kopf | |
| 7,361,806 B2 | 4/2008 | Lebel et al. | |
| 7,786,345 B2 | 8/2010 | Bae et al. | |
| 8,237,014 B2 | 8/2012 | Blaylock et al. | |
| 8,367,378 B2 | 2/2013 | Balan et al. | |
| 8,563,282 B2 | 10/2013 | Galvez, III et al. | |
| 9,085,745 B2 | 7/2015 | Eckelberry et al. | |
| 9,644,222 B2 | 5/2017 | Balan et al. | |
| 10,260,081 B2 * | 4/2019 | Singh ................... | C12P 19/02 |
| 11,492,649 B2 * | 11/2022 | Singh ................... | C12P 19/02 |
| 2010/0055741 A1 | 3/2010 | Galvez, III et al. | |
| 2011/0081689 A1 | 4/2011 | Flanegan et al. | |
| 2011/0129889 A1 | 6/2011 | Inamdar et al. | |
| 2011/0318796 A1 | 12/2011 | Walther | |
| 2012/0030840 A1 | 2/2012 | Miles | |
| 2012/0070874 A1 | 3/2012 | Kosugi et al. | |
| 2012/0220740 A1 | 8/2012 | Geremia et al. | |
| 2012/0252957 A1 | 10/2012 | Geremia et al. | |
| 2012/0258503 A1 | 10/2012 | Raab et al. | |
| 2013/0042859 A1 | 2/2013 | Geremia et al. | |
| 2013/0059346 A1 | 3/2013 | Medoff | |

(Continued)

FOREIGN PATENT DOCUMENTS

| | | |
|---|---|---|
| CN | 105229158 A | 1/2016 |
| EP | 2471940 A1 | 7/2012 |

(Continued)

OTHER PUBLICATIONS

U.S. Appl. No. 13/137,050, "U.S. Patent Application No.", Method for Recycling Enzyme, filed Jul. 18, 2011.
U.S. Appl. No. 14/775,588, "Advisory Action", dated May 10, 2018, 5 pages.
U.S. Appl. No. 14/775,588, "Final Office Action", dated Dec. 29, 2017, 15 pages.
U.S. Appl. No. 14/775,588, "Non-Final Office Action", dated Aug. 24, 2018, 14 pages.
U.S. Appl. No. 14/775,588, "Non-Final Office Action", dated Jul. 26, 2017, 11 pages.

(Continued)

*Primary Examiner* — Vera Afremova
(74) *Attorney, Agent, or Firm* — Kilpatrick Townsend & Stockton LLP

(57) ABSTRACT

The present disclosure provides methods for generating sugars from a cellulosic biomass. The methods combine treatment of the biomass using a high-shear milling device and saccharification of the biomass to partially hydrolyze the biomass. The biomass can be saccharified either after or simultaneously with the high-shear milling treatment. The partially hydrolyzed biomass is then separated into a solids stream with saccharification enzymes, and a liquid stream with sugars. The solids stream and associated enzymes are further incubated under saccharification conditions to produce additional sugars, or are recycled and added to fresh biomass, which is saccharified under high-shear milling conditions. The methods result in improved conversion of cellulosic biomass to glucose.

20 Claims, 21 Drawing Sheets

(56) References Cited

U.S. PATENT DOCUMENTS

2016/0032339 A1 2/2016 Singh et al.

FOREIGN PATENT DOCUMENTS

WO 2010025171 A1 3/2010
WO 2014144565 A1 9/2014

OTHER PUBLICATIONS

U.S. Appl. No. 14/775,588 , "Notice of Allowance", dated Dec. 18, 2018, 9 pages.
U.S. Appl. No. 14/775,588 , "Restriction Requirement", dated May 12, 2017, 7 pages.
U.S. Appl. No. 16/360,408 , "Advisory Action", dated Jul. 28, 2021, 5 pages.
U.S. Appl. No. 16/360,408 , "Final Office Action", dated Mar. 15, 2022, 9 pages.
U.S. Appl. No. 16/360,408 , "Final Office Action", dated May 3, 2021, 21 pages.
U.S. Appl. No. 16/360,408 , "Non-Final Office Action", dated Nov. 25, 2020, 17 pages.
U.S. Appl. No. 16/360,408 , "Non-Final Office Action", dated Sep. 2, 2021, 15 pages.
U.S. Appl. No. 16/360,408 , "Notice of Allowance", dated Jul. 1, 2022, 7 pages.
BR1120150233252 , "Notice of Allowance", dated Jan. 11, 2022.
BR1120150233252 , "Office Action", dated Nov. 16, 2021, 3 pages.
Chundawat , et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.
Chundawat , et al., "Multifaceted Characterization of Cell Wall Decomposition Products Formed during Ammonia Fiber Expansion (AFEX) and Dilute Acid Based Pretreatments", Biosource Technology, vol. 101, No. 21, Nov. 2010, pp. 8429-8438.
CN201480026922.8 , "Office Action", dated Apr. 3, 2018, 8 pages.
Gregg , et al., "Factors Affecting Cellulose Hydrolysis and the Potential of Enzyme Recycle to Enhance the Efficiency of an Integrated wood to Ethanol Process", Biotechnology and Bioengineering, vol. 51, No. 4, Aug. 20, 1996, pp. 375-383.
Jin , et al., "A Novel Integrated Biological Process for Cellulosic Ethanol Production Featuring High Ethanol Productivity, Enzyme Recycling and Yeast Cells Reuse", Energy & Environmental Science, Issue 5, Mar. 13, 2012, pp. 7168-7175.
Khullar , et al., "Effect of Particle Size on Enzymatic Hydrolysis of Pretreated Miscanthus", Industrial Crops and Products, vol. 44, Jan. 2013, pp. 11-17.
PCT/US2014/029032 , "International Search Report and Written Opinion", dated Jul. 24, 2014, 12 pages.

* cited by examiner

CELLULOSIC ENZYME RECYCLING FROM SEPARATION OF SACCHARIFIED BIOMASS

CROSS-REFERENCE TO RELATED PATENT APPLICATIONS

The present application is a continuation of Non-provisional application Ser. No. 16/360,408 filed Mar. 21, 2019, which is a divisional of Non-provisional application Ser. No. 14/775,588 filed Sep. 11, 2015, now U.S. Pat. No. 10,260,081, which is a 371 National Phase of International Application No. PCT/US2014/029032 filed Mar. 14, 2014 which claims the benefit of priority to US Provisional Patent Application No. 61/798,070, filed Mar. 15, 2013, each of which is incorporated by reference herein in its entirety.

BACKGROUND OF THE INVENTION

Enzymatic hydrolysis is an important step for the biomass-based biofuel production. Enzymatic hydrolysis eliminates the need for large quantities of acid and the neutralization of this acid, but commercial cellulase enzyme costs are currently high, and enzyme attack of the cellulose and hemicellulose polymers can be slow. On the other hand, many details of enzymatic activity are still poorly understood, although the mechanisms of hydrolysis and the relationship between the structure and function of various cellulases have been extensively studied.

The enzymatic hydrolysis of lignocellulosic substrates is strongly affected by end product inhibition and enzyme features. Therefore, biomass hydrolysis is directly or indirectly related to the substrate availability, end product accumulation and/or enzyme inhibitors generated during or after biomass pretreatment which hinders the specific activities of cellulases on their respective substrates. Low specific catalyst activity on substrates limits the effectiveness of hydrolysis.

BRIEF SUMMARY OF THE INVENTION

The present methods are directed to improving the saccharification of cellulosic biomass to generate sugars that can be converted to useful downstream products, such as biofuel. In the method, biomass is contacted with a catalyst under conditions suitable to hydrolyze components of the biomass to sugars. In some embodiments, the conditions include contacting the biomass with a catalyst under conditions of high-shear agitation. In some embodiments, the biomass is treated with a high shear milling device to produce a relatively uniform particle size prior to contacting the biomass with a catalyst to hydrolyze components of the biomass to sugars. The resulting hydrolyzed biomass mixture is separated into a liquid stream comprising sugars and a solids stream comprising solids where both phases constitute residual enzymes, which are described in the embodiments of this document. In some embodiments, the separation step occurs after partial hydrolysis of the biomass. The solids are further incubated under conditions suitable to hydrolyze components of the solids to sugars, thereby producing additional sugars. In some embodiments, the method converts at least 80% of the glucan in the biomass to glucose in about 6 to about 24 hours.

Thus, in one aspect, a method is described for generating sugars from biomass, the method comprising:
(a) contacting the biomass with a catalyst under conditions of high-shear agitation suitable to hydrolyze components of the biomass to sugars, thereby producing a mixture of solids and a liquid comprising sugars;
(b) separating the mixture into a liquid stream comprising sugars and a solids stream comprising solids;
(c) incubating the solids under conditions suitable to hydrolyze components of the solids to sugars, thereby producing additional sugars.

In another aspect, a method is described for generating sugars from biomass, the method comprising:
(a) pretreating the biomass with a high shear/milling mixing device comprising a rotor and a stator, wherein the high shear; milling mixing device has a gap setting between the rotor and stator of between about 0.1 and 2.2 millimeters, thereby reducing the size of biomass particles in the biomass;
(b) contacting the biomass with a catalyst to hydrolyze components of the biomass to sugars, thereby producing a mixture of solids and a liquid comprising sugars;
(c) separating the mixture into a liquid stream comprising sugars and a solids stream comprising solids;
(d) incubating the solids stream under conditions suitable to hydrolyze components of the solids to sugars, thereby producing additional sugars.

In some embodiments of the above aspects, the biomass comprises glucan and at least 80% of the glucan in the biomass is hydrolyzed to glucose in about 6 to about 24 hours. In some embodiments, the biomass is a lignocellulosic biomass. The biomass can comprise at least about 10% solids w/w prior to contacting the biomass with the catalyst. The biomass can also be pretreated before contacting the biomass with the catalyst. The catalyst can comprise an enzyme, such as a hydrolytic enzyme, or can be a non-enzymatic catalyst.

In some embodiments, the conditions of high-shear agitation produce a biomass particle size wherein at least about 80% of the particles have a particle size of from about 1 to about 800 microns, from about 2 to about 600 microns, from about 2 to about 400 microns, or from about 2 to about 200 microns.

In some embodiments, the mixture is separated using a mechanical device, a filter, a membrane, or a tangential flow filtration device. The mechanical device can be a centrifuge, a press, or a screen.

In some embodiments, the biomass mixture is partially hydrolyzed for various lengths of time prior to separating the mixture into a liquid stream and a solids stream. For example, in some embodiments, the separating step occurs at about 2 to about 4 hours, or at about 4 to about 6 hours after contacting the biomass with a catalyst. In one embodiment, the biomass mixture is separated into a liquid stream and a solids stream when about 30% to about 60% of the glucan present in the biomass is converted to glucose. The methods described herein result in an increase in the amount of glucan converted to glucose compared to a method that does not comprise the step of separating the mixture into a liquid stream and a solids stream; and incubating the solids stream under conditions suitable to hydrolyze components of the solids to sugars. In some embodiments, the amount of glucan converted is at least 10% greater than the amount of glucan converted when compared to a method that does not include the additional separating and incubating steps.

In some embodiments, the solids stream is incubated under conditions suitable to hydrolyze components of the solids to sugars for about 8 to about 20 hours. The solids stream can also be incubated under conditions of high shear agitation.

In some embodiments, the solids stream is contacted with additional biomass in a batch, semi-batch, or continuous process. The additional biomass can also comprise a catalyst that hydrolyzes components of the biomass to sugars.

In some embodiments, the sugars produced by the methods are processed into ethanol, biofuels, biochemicals, or other chemical products. In some embodiments the liquid stream that is separated from the biomass mixture comprises increased amounts of compounds such as furfural, oligosaccharides and phenolics compared to biomass that is not treated according to the present methods. In some embodiments, the hydrolyzed components of the biomass contain decreased concentrations of contaminants compared to biomass that is not treated under high shear conditions.

In some embodiments, the biomass is contacted with a catalyst suitable to hydrolyze components of the biomass to sugars after the biomass is treated with a high shear device.

In some embodiments, the conditions of high shear agitation comprise treating the biomass with a high shear/milling mixing device comprising, a rotor and a stator. The gap setting between the rotor and stator can be between about 0.1 and about 2.2 millimeters, depending on the type of biomass used.

In one embodiment, the method further comprises separating the liquid stream into a second liquid stream comprising sugars and a second solid stream comprising solids; and incubating the second solids under conditions suitable to hydrolyze components of the solids to sugars, thereby producing additional sugars.

In some embodiments, the biomass is mixed with water to provide a biomass/water mixture prior to the pretreatment step or prior to contacting the biomass with a high shear milling device.

Further embodiments of the invention are described herein.

Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "catalyst" refers to a compound or substance that increases the rate of a chemical reaction, such as the hydrolysis of cellulose, or allows the reaction to proceed at substantially the same rate at a lower temperature. The term includes hydrolytic and saccharification enzymes that convert lignocellulosic biomass to polysaccharides, oligosaccharides, and/or simple fermentable sugars. The term also includes saccharification enzymes that are produced by genetically engineered or transgenic plants, for example, as described in U.S. Patent Publication 2012/0258503 to Rabb et al., which is incorporated by reference herein in its entirety. The term also includes polymeric acid catalysts, for example, as described in U.S. Patent Publications 2012/0220740, 2012/0252957, and 2013/0042859, which are each incorporated by reference herein in their entirety.

The term "biomass" refers to any material comprising lignocellulosic material. Lignocellulosic materials are composed of three main components: cellulose, hemicellulose, and lignin. Cellulose and hemicellulose contain carbohydrates including polysaccharides and oligosaccharides, and can be combined with additional components, such as protein and/or lipid. Examples of biomass include agricultural products such as grains, e.g., corn, wheat and barley; sugarcane; corn stover, corn cobs, bagasse, sorghum and other inedible waste parts of food plants; food waste; grasses such as switchgrass; and forestry biomass, such as wood, paper, board and waste wood products.

The term "lignocellulosic" refers to material comprising both lignin and cellulose, and may also contain hemicellulose.

The term "cellulosic," in reference to a material or composition, refers to a material comprising cellulose.

The term "glucan" refers to all alpha and beta-linked 1,4, homopolymers of glucose subunits The term "conditions suitable to hydrolyze components of the biomass to sugars" refers to contacting the solids phase biomass with one or more catalysts including, but not limited to, cellulase, hemicellulase and auxiliary enzymes or proteins in order to produce fermentable sugars and shorter chain sugar oligosaccharides from polysaccharides in the biomass. The conditions can further include a pH that is optimal for the activity of saccharification enzymes, for example, a pH range of about 4.0 to about 7.0. The conditions can further include a temperature that is optimal for the activity of catalysts, including saccharification enzymes, for example, a temperature range of about 20° C. to 100° C., about 35° C. to 75° C. or about 40° C. to 60° C.

The terms "high-shear agitation," "high-shear mixing," and "high-shear milling" or "high shear milling/saccharification" refer to subjecting the biomass to conditions of high shear in order to reduce the biomass particle size and/or enhance the mixing of the biomass mixture including catalysts. In some embodiments, the conditions produce a biomass particle size distribution from about 1 to about 800 microns. In some embodiments, the biomass particle size distribution is such that at least about 70%, 75%, 80%, 85%, 90%, or 95% of the particles have a size of from about 1 to about 800 microns, from about 2 to about 600 microns, from about 2 to about 400 microns, or from about 2 to about 200 microns. High-shear conditions can be provided by devices well known in the art, for example, by an ICS-type orifice reactor (Buchen-Industrial Catalyst Service), a rotating colloidal-type mill, a Silverson mixer, cavitation milling device, auger, milling auger, or steam assisted hydro jet type mill. In some embodiments the high shear devices include any device with a stationary stator and a rotating rotor positions to maintain a physical gap between the rotor and the stator during operation such that a high shear zone is generated within this gap or along this gap. In some embodiments the high shear devices comprises an auger milling device with milling rods or bars inserted between auger flights and contained within slots in the auger flights that allow the rods to travel between the center and the wall region of the auger diameter. As the auger rotates, the milling rods travel to the center of the auger assembly at the top of the rotation defined as zero degree position. The bar drops toward the outside diameter or wall of the auger assembly, as the rotation progresses passed the 90 degree and toward the 180 degree rotation position, such that this movement produces a milling action caused by the mass of the rod hitting the biomass as it travels along the lower region of the auger due to the rotation of the auger flights. The auger bars can be equipped with various surface features to support effective milling of the biomass and can be positions at various locations along the auger flights to maintain balance during rotation and optimum conditions for conversion of the biomass. These high shear milling devices can be used before and or during the process steps of pretreatment and saccharification in any combination to enhance the conversion of the biomass to sugars.

The term "saccharification," also referred to as "hydrolysis," refers to production of sugars and short chain sugar oligomers from biomass or biomass feedstock or feedstock comprising non-cellulosic biomass. Saccharification can be accomplished by catalysts including hydrolytic enzymes, cellulases, alpha amylases, gluco-amylases, beta-glucosidases, and/or auxiliary proteins, including, but not limited to, peroxidases, laccases, expansins and swollenins. "Hydrolysis" refers to breaking the glycosidic bonds in polysaccharides and the incorporation of a water to yield simple monomeric and/or oligomeric sugars. For example, hydrolysis of cellulose produces the six carbon (C6) sugar such as glucose and glucose oligomers, whereas hydrolysis of hemicellulose produces both the five carbon (C5) sugars such as xylose and arabinose and the six carbon (C6) sugars such as galactose and mannose and various oligomers. Generating short chain cellulosic sugars from polymer cellulosic fibers and biomass can be achieved by a variety of techniques, processes, and/or methods. For example, cellulose can be hydrolyzed with water to generate cellulosic sugars. Hydrolysis can be assisted and or accelerated with the use of hydrolytic enzymes, chemicals, mechanical shear, thermal and pressure environments, and or any combination of these techniques. Examples of hydrolytic enzymes include β-glucosidase, xylanase, cellulases and hemicellulases. Cellulase is a generic term for a multi-enzyme mixture including exo-cellobiohydrolases, endoglucanases and β-glucosidases which work in combination to hydrolyze cellulose to cellobiose and glucose. Examples of chemicals include strong acids, weak acids, weak bases, strong bases, ammonia, or other chemicals. Mechanical shear includes high shear orifice, cavitation, colloidal milling, and auger milling.

The term "fermentable sugar" refers to a sugar that can be converted to ethanol or other products such as but not limited to methanol, butanols, propanols, succinic acid, and isoprene, during fermentation, for example during fermentation by yeast. For example, glucose is a fermentable sugar derived from hydrolysis of cellulose, whereas xylose, arabinose, mannose and galactose are fermentable sugars derived from hydrolysis of hemicellulose.

The term "simultaneous saccharification and fermentation" (SSF) refers to a process in which fermentable sugars are generated through the enzymatic hydrolysis of biomass while the same sugars are consumed, almost immediately, during fermentation to produce valuable products such as biofuels. This is in contrast to the term "separate hydrolysis and fermentation" (SHF), where biomass hydrolysis with enzymes precedes the fermentative conversion of sugars.

The term "pretreatment" refers to treating the biomass with physical, thermal, chemical or biological means, or any combination thereof, to render the biomass more susceptible to hydrolysis, saccharification, or conversion to sugars and short chain sugar oligomers, for example, by saccharification enzymes. Pretreatment can comprise treating the biomass at elevated pressures and/or elevated temperatures. Pretreatment can further comprise physically mixing and/or milling the biomass in order to reduce the size of the biomass particles and to produce a uniform particle size. Devices that are useful for physical pretreatment of biomass include, e.g., a hammermill, shear mill, cavitation mill colloid mill or other high-shear mill, or auger mill. An exemplary colloid mill is the Cellunator™ (Edeniq, Inc., Visalia. CA). The use of a high-shear colloid mill to both reduce particle size and produce a uniform particle size to improve ethanol yields is described in, for example, WO2010/025171, which is incorporated by reference herein in its entirety.

The term "elevated pressure," in the context of a pretreatment step, refers to a pressure above atmospheric pressure (e.g., 1 atm at sea level or 14,695 psi) based on the elevation, for example at least 20, 30, 40, 50, 60, 70, 80, 90, 100, 110, 120, 130, 140, 150, 200, 220 psi or greater at sea level. In some embodiments, such as but not limited to high shear orifice milling, "elevated pressure" can be very high pressures such as 67, 133, 200, 400, 700 atm (985 to 10,300 psi) or greater.

The term "elevated temperature," in the context of a pretreatment step, refers to a temperature above ambient temperature, for example at least 100, 110, 120, 130, 140, 150, 160, 170, 180, 190, 200, 210, 250 degrees C. or greater. When used in hydrothermal pretreatment, the term includes temperatures sufficient to substantially increase the pressure in a closed system. For example, the temperature in a closed system can be increased to 170° C. and above such that the pressure is at least 100 psi or greater, such as 131, 167, 211, 262, 570 psi or greater.

The term "pretreated biomass" refers to biomass that has been subjected to pretreatment to render the biomass more susceptible to hydrolysis.

DETAILED DESCRIPTION OF THE INVENTION

Figure 1:
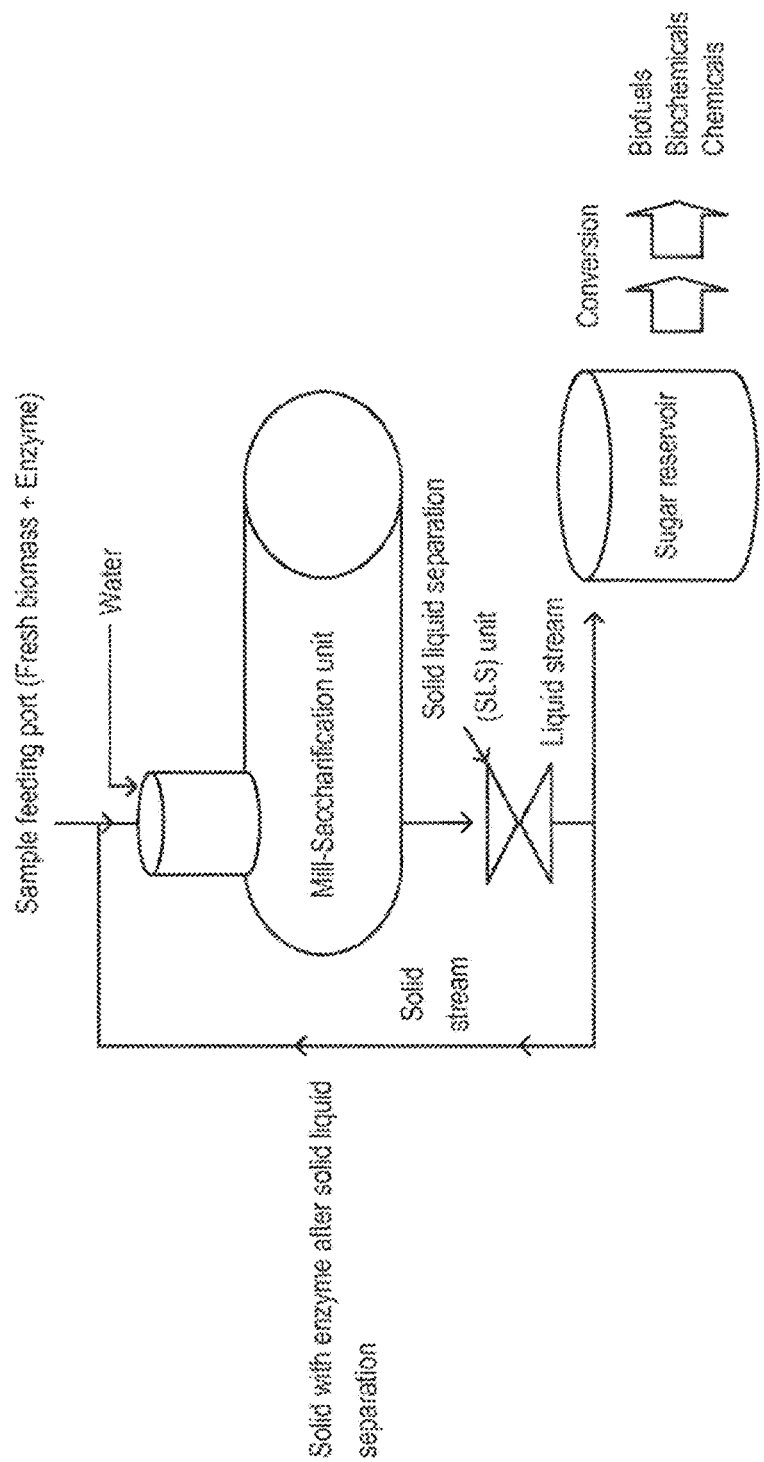
FIG. 1 shows one illustrative embodiment of the method described herein.

The methods described herein have surprisingly been found to increase the conversion rate of cellulosic biomass to sugars by combining high-shear milling with saccharification, and separating the partially hydrolyzed biomass solids from the liquids before the saccharification is complete. The present disclosure describes methods that are useful for generating sugars from biomass. In one aspect, the methods comprise treating the biomass with a high shear milling device to produce a relatively uniform particle size, followed by contacting the treated biomass with a catalyst under conditions suitable to hydrolyze components of the biomass to sugars. In another aspect, the methods comprise contacting the biomass with a catalyst under conditions of high-shear agitation (e.g., high-shear mixing or high-shear milling). The conditions are suitable to hydrolyze components of the biomass to sugars. Thus, the conditions produce a mixture of solids and a liquid comprising sugars. The high-shear agitation conditions are allowed to proceed for a defined period of time such that at least a portion of the biomass is hydrolyzed to sugars. For example, in some embodiments, the conditions are allowed to proceed for a period of time sufficient to produce a biomass particle size distribution such that at least about 80% (e.g., at least 80%, 85%, 90%, 95%, or greater) of the biomass particles are from about 2 to about 200 microns. In some embodiments, the period of time is about 2-4 hours. In some embodiments, the period of time is about 4-6 hours. In some embodiments, the period of time is about 6-8 hours. In some embodiments, the period of time is about 8 to 10 hours. In some embodiments, the period of time is no greater than 10 hours. In some embodiments, the period of time is about 1, 2, 4, 6, 8 or 10 hours.

After the biomass is hydrolyzed into a mixture, the hydrolyzed mixture is separated into a liquid stream comprising sugars and a stream comprising solids (i.e., a "solids stream"). As will be understood by a person of skill in the art, a solids stream typically comprises other components, such as a liquid (e.g., an aqueous liquid, or water), dissolved solids, residual sugars, and/or hydrolytic enzymes. The separation step can be performed using any suitable method known in the art. For example, in some embodiments, the separation step is performed using a mechanical device, a filter, a membrane, or a tangential flow filtration device. In some embodiments the mechanical device is a centrifuge, a press, or a screen. Examples of separation methods and devices are further described herein.

The separation step can occur after a suitable period of time described herein. For example, the separation step can occur at about 1 to about 2 hours after the biomass is contacted with the catalyst and subjected to high-shear agitation. In some embodiments, the separation step can occur at about 2 to about 4 hours after the biomass is contacted with the catalyst and subjected to high-shear agitation. In some embodiments, the separation step can occur at about 4 to about 6 hours after the biomass is contacted with the catalyst and subjected to high-shear agitation. In some embodiments, the separation step can occur at about 6 to about 8 hours after the biomass is contacted with the catalyst and subjected to high-shear agitation. In some embodiments, the separation step can occur at about 8 to about 10 hours after the biomass is contacted with the catalyst and subjected to high-shear agitation. In some embodiments, the separation step is performed no later than 10 hours after the biomass is first contacted with the catalyst and subjected to high-shear agitation. In some embodiments, the separation step is performed at about 1, 2, 4, 6, 8 or 10 hours after the biomass is contacted with the catalyst and subjected to high-shear agitation. In some embodiments, the separation step is performed after a period of time sufficient to convert about 30% to about 60% w/v of the glucan in the biomass to glucose. Thus, in some embodiments, the separation step occurs when about 30%, 35%, 40%, 45%, 50%, 55%, or 60% of the glucan is converted to glucose.

After the separation step, the solids are incubated under conditions suitable to hydrolyze components of the solids to sugars. This further hydrolysis produces additional sugars. In some embodiments, at least about 80% of the glucan in the biomass is converted to glucose in about 6 to about 24 hours, or in about 6 to about 18, or about 6 to about 12, or about 6 to about 10, or about 6 to about 8 hours. In some embodiments, the incubation step is no greater than about 6, 7, 8, 9, 10, 11, 12, 13, 14, 15, 16, 17, 18, 19, 20, 21, 22, 23, or 24 hours. In some embodiments, the amount of glucan converted is at least 10%, 15%, 20%, 25%, 30%, 40%, or 50% greater than the amount of glucan converted when compared to a method that does not comprise the separating step described herein.

It will be understood that the conversion of glucan to glucose can occur during both the first hydrolysis step (under conditions of high-shear agitation or following the application of high shear agitation) and after the separating step. Thus, the total amount of glucan converted to glucose can include the glucose produced during both the first hydrolysis step and after the separating step. In some embodiments, the total hydrolysis time (i.e., combined first hydrolysis step and after the separating step) sufficient to convert 80% of the glucan to glucose is no greater than about 6, 7, 8, 9, 10, 11, 12, 13, 14, 15, 16, 17, 18, 19, 20, 21, 22, 23, or 24 hours.

In some embodiments, the conditions suitable to hydrolyze components of the solids to sugars include incubating the solids under high-shear agitation or high-shear mixing conditions or following the application of high shear agitation. For example, in one embodiment, the solids are incubated in a second high-shear agitation device. In some embodiments, the solids are added to and incubated in the same high-shear agitation device that contains the biomass.

In some embodiments, the biomass is a lignocellulosic biomass. Examples of biomass useful in the methods described herein include, but are not limited to, agricultural crops, forest crops, and different types of waste and byproducts that contain lignocellulose and/or cellulose. Biomass includes, but is not limited to, agricultural biomass such as corn stover, corn cobs, corn husks, wheat straw, rice straw, rice hulls, barley straw, oat straw, oat hulls, canola straw, and soybean stover; grasses such as switchgrass, miscanthus, cord grass, rye grass, and reed canary grass; sugar cane and sugar processing byproducts, such as bagasse and beet pulp; sorghum, wood products, trees and parts thereof, sawdust, recycled pulp fiber, wood chips, newsprint, and cardboard; and animal waste. The biomass may also comprise a processed lignocellulosic feedstock.

In some embodiments, the biomass comprises at least about 10%, 15%, 20%, 25%, or 30% solids (w/w) prior to being contacted with the catalyst. In some embodiments, the biomass is a pretreated biomass. Suitable pretreatment conditions are described herein.

In some embodiments, the solids that are separated from the mixture are contacted with additional biomass. The solids can be incubated under hydrolysis conditions for a period a time before contacting the biomass, or can be immediately contacted with the biomass. In some embodiments, the solids comprise hydrolytic enzymes that are recycled back into contact with the biomass. Recycling of enzymes has the advantage of reducing the amount of enzymes that need to be added to fresh biomass in order to hydrolyze cellulose. The biomass that is contacted with the solids can be fresh biomass (e.g., biomass that has not been contacted with a catalyst, or biomass that has been contacted with a catalyst to produce a mixture of solids and a liquid comprising sugars, but prior to separating the mixture into a liquid stream and a solids stream), or can be a portion of the original biomass that produced the solids. The solids and associated enzymes can be contacted with additional biomass in a batch, semi-batch, or continuous process. In some embodiments, the additional biomass further comprises a catalyst that is capable of hydrolyzing components of the biomass to sugars. In some embodiments, the solids are contacted with the additional biomass under conditions of high-shear agitation (e.g., in a high shear reactor).

In an embodiment of a continuous process, the solids are added to new or fresh biomass in a high-shear agitation device, and the new biomass and solids are incubated under conditions suitable to produce sugars. To determine the amount of biomass glucan converted into glucose, the rate at which biomass is added into the high-shear milling device is measured, and the average net rate of glucose produced is determined. Thus, in some embodiments of a continuous process, the conversion of glucan to glucose is a steady state level or rate. In one embodiment, the glucan conversion rate is determined by calculating the amount of glucose produced as a percentage of the glucose equivalent of the glucan in the biomass per unit time, fed to the continuous process.

In some embodiments, the sugars in the liquid stream separated from the mixture and/or the additional sugars produced during the incubation step of the solids are processed into ethanol, biofuels, biochemicals, or other chemical products.

In some embodiments, the liquid stream that is separated from the mixture comprises increased amounts of compounds such as, but not limited to, furfural, oligosaccharides, and short-chain phenolics as compared to biomass that is not treated with the catalyst under conditions of high-shear agitation. These compounds can provide additional sources of revenue for an ethanol facility. Thus, in some embodiments, the liquid stream that is separated from the mixture comprises at least 5%, 10%, 15%, 20%, or more of the compounds as compared to a liquid stream separated from a biomass mixture that is not treated with the catalyst wider conditions of high-shear agitation.

In some embodiments, the hydrolyzed components of the solids are separated into a second solids stream and a second liquids stream comprising the additional sugars. In some embodiments, the second liquid stream contains decreased concentrations of contaminants compared to biomass that is not treated with the catalyst under conditions of high-shear agitation. The contaminants can include inhibitors of saccharification and/or fermentation. Thus, in some embodiments, the second liquid stream contains at least 5%, 10%, 15%, 20% or less concentration of contaminants compared to a liquid stream separated from hydrolyzed components of the solids, wherein the solids were separated from a hydrolyzed mixture that is not treated with the catalyst under conditions of high-shear agitation.

Pretreatment

Prior to the hydrolysis steps described herein, the biomass can be pretreated to render the lignocellulose and cellulose more susceptible to hydrolysis. Pretreatment includes treating the biomass with physical, chemical or biological means, or any combination thereof, to render the biomass more susceptible to hydrolysis, for example, by saccharification enzymes or the catalysts described herein. Examples of chemical pretreatment are known in the art, and include acid pretreatment and alkali pretreatment.

One example of physical pretreatment includes elevated temperature and elevated pressure. Thus, in some embodiments, pretreatment comprises subjecting the biomass to elevated temperatures and elevated pressure in order to render the lignocellulose and cellulose accessible to enzymatic hydrolysis. In some embodiments, the temperature and pressure are increased to amounts and for a time sufficient to render the cellulose susceptible to hydrolysis. In some embodiments, the pretreatment conditions can comprise a temperature in the range of about 150° C. to about 210° C. The pretreatment temperature can be varied based on the duration of the pretreatment step. For example, for a pretreatment duration of about 60 minutes, the temperature is about 160 degrees C.; for a duration of 30 minutes, the temperature is about 170 degrees C.; for a duration of 5 minutes, the temperature is about 210 degrees C.

The pretreatment conditions can also comprise increased pressure. For example, in some embodiments, the pressure can be at least 100 psi or greater, such as 110, 120, 130, 140, 150, 200, 265 psi or greater. In some embodiments, the biomass is pretreated in a closed system, and the temperature is increased in an amount sufficient to provide the desired pressure. In one embodiment, the temperature is increased in the closed system until the pressure is increased to about 125, to about 145 psi, or about 265 psi. Persons of skill in the art will understand that the temperature increase necessary to increase the pressure to the desired level will depend on various factors, such as the size of the closed system and the equilibrium of saturated steam. In some embodiments, pretreatment comprises any other method known in the art that renders lignocellulose and cellulose more susceptible to hydrolysis, for example, acid treatment, alkali treatment, and steam treatment, or combinations thereof.

In some embodiments, the pretreatment step does not, result in the production of a substantial amount of sugars. For example, in some embodiments, pretreatment results in the production of less than about 10%, 5%, 1%, 0.1%, 0.01%, or 0.001% by weight glucose, less than about 10%, 5%, 1%, 0.1%, 0.01%, or 0.001% by weight xylose, and/or less than about 10%, 5%, 1%, 0.1%, 0.01%, or 0.001% by weight sugars in general. In some embodiments, the amount of sugars in the process stream entering the pretreatment stage is substantially the same as the amount of sugars in the process stream exiting the pretreatment stage. For example, in some embodiments, the difference between the amount of sugars in the process stream entering the pretreatment stage and the amount of sugars exiting the pretreatment stage is less than about 10%, 5%, 1%, 0.1%, 0.01%, or 0.001% by weight.

In some embodiments, pretreatment can further comprise physically mixing and/or milling the biomass in order to reduce the size of the biomass particles. The yield of biofuel (e.g., ethanol) or fermentable sugars can be improved by using biomass particles having relatively small sizes. Devices that are useful for physical pretreatment of biomass include, e.g., a hammermill, shear mill, cavitation mill or colloid or any other style or configuration of a high shear mill. Thus, in some embodiments, the pretreatment step comprises physically treating biomass with a colloid mill. An exemplary colloid mill is the Cellunator™ (Edeniq, Visalia, CA). In some embodiments, the biomass is physically pretreated to produce particles having a relatively uniform particle size of less than about 1600 microns. For example, at least about 50%, 60%, 70%, 80%, 85%, 90%, or 95% of the pretreated biomass particles can have a particle size from about 100 microns to about 800 microns. In some embodiments, at least about 50%, 60%, 70%, 80%, 85%, 90%, or 95% of the pretreated biomass particles have a particle size from about 100 microns to about 500 microns. In some embodiments, the biomass is physically pretreated to produce particles having a relatively uniform particle size using a colloid mill. The use of a colloid mill to produce biomass particles having a relatively uniform particle size, e.g., from about 10 microns to about 800 microns, can result in increased yield of sugars, as described in U.S. Patent Application Publication No. 2010/0055741 (Galvez et al.), which is incorporated by reference herein in its entirety.

Colloid mills are available in various sizes and materials of construction. A person skilled in the art would be able to optimize the size and metallurgy for various biomass. For example two IKA model MK2000/50 can be utilized in duplex stainless steel for a 50 MMGPY (million gallons per year) corn fermentation process while a single IKA model MK2000/50 comprised of 304 stainless steel parts is all that is required for a 30 MMGPY sugar cane cellulosic process. In each instance, gap size is optimized for the various feedstock material input as well as various flow rate conditions.

A colloid mill can be used to pretreat biomass, such as corn biomass. In some embodiments, pretreatment with a colloid mill can improve the yield of ethanol production when compared to pretreatment with a hammer mill alone. The colloid mill can be retrofitted, for example in current corn ethanol production plant by being inserted in-line between a mix tank and a liquefaction tank. The colloid mill can also be used in designing and building new biofuels production plants.

The colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 10-800 microns. For example, in some embodiments, a gap setting of 0.1-0.15 is used for corn stover or other cellulosic biomass and a gap setting of 0.2-0.3 mm is used for grains including but not limited to corn kernels. In other embodiments, for example with cellulosic biomass such as bagasse, the gap setting can range from 1.1-2.2 millimeters, e.g., 1.1-1.9 millimeters, e.g., from 1.4-1.9 millimeters. A colloid mill can be used to produce relatively precise, uniform particles sizes with high surface area which results in a greater percent of starch, cellulose and sugar being available for enzymatic conversion than a hammer mill, leading to improved yield.

Typically, as discussed earlier, the finer the biomass the better the attained yield with respect to gallons of biofuel per ton of biomass. However, a serious overriding factor in the overall process is the recovery of residual solids after the biofuel has been removed. This factor as explained above results in an optimal biomass size of 100-500 microns for corn ethanol. For cellulosic processes that utilize rice straw, sugar cane, energy cane and other materials (such as those described herein) where state of the art filtration equipment can be installed, biomass size can be from 50-350 microns, typically from 75-150 microns.

The weight range of solids in the corn mash in most biofuels plants is 25-35 wt % (db). A colloidal mill placed in-line between a mix tank and a liquefaction tank can tolerate the entire range of solids typically encountered and, due to the high uniformity of particle size and lower fluid viscosities achieved, also allows for higher loadings of biomass (e.g., in the range of 40 wt %) than a similar process in the absence of a colloid mill.

In some instances, biomass can be introduced directly into a colloid mill. In other instances, however, the biomass undergoes one or more pretreatment steps prior to being introduced into the colloid mill. For example, the biomass can be pretreated first with a communition device (e.g., a hammer mill, macerator), which generally breaks apart the biomass and results in a large and random distribution of particle sizes, which is later followed by a more precise grinding using a colloidal mill or a macerator followed by a colloid mill, which results in relatively uniform particles of a desired size. For example, biomass from different materials, such as but not limited to, corn and rice straw can be fed through a hammer mill with a fixed set of sieve sizes such as #7 or #8. The hammer mill can then be coupled to a colloidal mill with an adjustable gap setting for dynamically dialing in the desired particle size of the biomass.

In some embodiments, the pretreatment step does not involve the use of acids which can degrade sugars into inhibitors of fermentation.

In some embodiments, the pH of the pretreated biomass is adjusted to a pH of between about 3.0 and about 6.5. In some embodiments, the pH of the biomass is adjusted during or after the pretreatment step to be within the optimal range for activity of saccharification enzymes, e.g., within the range of about 4.0 to 6.0. In some embodiments, the pH of the biomass is adjusted using $Mg(OH)_2$, $NH_4OH$, $NH_3$, or a combination of $Mg(OH)_2$ and $NH_4OH$ or $NH_3$.

After pretreatment, the pretreated biomass is hydrolyzed to produce sugars using the methods and catalysts described herein.

Examples of Catalysts

The catalysts used in the methods include saccharification enzymes and various combinations thereof. Examples of saccharification enzymes include glycosidases, cellulases, hemicellulases, starch-hydrolyzing glycosidases, xylanases, ligninases, and feruloyl esterases, and combinations thereof. Glycosidases hydrolyze the ether linkages of di-, oligo-, and polysaccharides. The term cellulase is a generic term for a group of glycosidase enzymes which hydrolyze cellulose to glucose, cellobiose, and other cello-oligosaccharides. Cellulase can include a mixture comprising exo-cellobiohydrolases (CBH), endoglucanases (EG) and β-glucosidases (BG). Hemicellulase is a generic term for a group of glycosidase enzymes which hydrolyze hemicellulose to xylose and other oligosaccharides. Hemicellulase can include xylanases, endoxylanases, exoxylanases, β-xylosidases, arabinoxylanases, mannases, galactases, pectinases, and glucuronidases. Saccharification enzymes also include starch-hydrolyzing glycosidases, such as but not limited to amylases, α-amylases, β-amylases, glucoamylases, α-glucosidases, and isoamylases. Specific examples of saccharification enzymes include carboxymethyl cellulase, xylanase, β-glucosidase, β-xylosidase, and α-L-arabinofuranosidase, and amylases. Saccharification enzymes are commercially available, for example. Cellic® CTec2 and HTec2 or CTecIII (Novozymes, Denmark), Accellerase® and Accellerase Trio® (DuPont Industrial Biosciences, Rochester, N.Y.), CodeXyme® 4 (Codexis) and Multifect® xylanase (DuPont Industrial Biosciences). Saccharification enzymes can also be expressed by host organisms, including recombinant microorganisms. In some embodiments, the saccharification enzymes are produced by genetically engineered or transgenic plants, for example, as described in U.S. Patent Publication 2012/0258503 to Rabb et al., which is incorporated by reference herein in its entirety.

In some embodiments, the catalyst is a polymer comprising acidic monomers and ionic monomers, wherein each acidic monomer has at least one Bronsted-Lowry acid, and each ionic monomer independently has at least one nitrogen-containing cationic group or phosphorous-containing cationic group. In some embodiments, the Bronsted-Lowry acid is selected from the group consisting of sulfonic acid, phosphonic acid, acetic acid, isophthalic acid, boronic acid, and perfluorinated acid. Examples of suitable polymeric acid catalysts are described in U.S. Patent Publications 2012/0220740, 2012/0252957, and 2013/0042859, which are each incorporated by reference herein in their entirety.

Solid Liquid Separation and Enzyme Recycling Methods

The methods described herein make use of various types of separators and separation methods. The solid stream separated by the separators will contain the partially hydrolyzed biomass embedded with hydrolytic enzymes which are recycled in a continuous fashion during the saccharification process. The liquid streams are further passed through membrane separator units to separate the small solids from the liquid containing part of the hydrolytic enzymes. In some embodiments, the separator is a mechanical device, including but not limited to a centrifuge, a decanter centrifuge, a disk stack centrifuge, or a press. In some embodiments, the separator is a filter, such as filter press, Vincent type press, cylinder press or sand-type filter. In some embodiments, the separator is a screen type separator. Non-limiting examples of screen type separators include screens, vibrating screens, reciprocating screens (rake screens), gyratory screens/sifters, and pressure screens.

In some embodiments, the separator is a membrane type separator. Membranes are used for further separating smaller biomass solids and polysaccharides and or disaccharides and or monosaccharides and or lignin and or hemicellulose and or xylose and or arabinose and or mannose and or galactose etc. from the enzyme stream while concentrating enzymes containing exoglucanases, endoglucanases, betaglucosidase, endo xylanases, xylosidase, mannases, arabinases, pectinases etc. to be recycled back in the system. Examples of membrane type separators include ultrafiltration (UF) membranes, microfiltration (MF) membranes, and Tangential Flow Filtration (TFF) systems and hollow-fiber filtration systems which are engineered to perform MF or UF filtrations.

MF membranes typically have a pore size of between 0.1 micron and 10 microns. Examples of microfiltration membranes include glass microfiber membranes such as Whatman GF/A membranes. UF membranes have smaller pore sizes than MF membranes, typically in the range of 0.001 to 0.1 micron. UF membranes are typically classified by molecular weight cutoff (MWCO). Examples of ultrafiltration membranes include polyethersulfone (PES) membranes having a low molecular weight cutoff, for example about 10 kDa. UF membranes are commercially available, for example from Synder Filtration (Vacaville, CA).

Filtration using either MF or UF membranes can be employed in direct flow filtration (DFF) or Tangential Flow Filtration (TFF). DFF, also known as dead end filtration, applies the feed stream perpendicular to the membrane face such that most or all of the fluid passes through the membrane. TFF, also referred to as cross-flow filtration, applies the feed stream parallel to the membrane face such that one portion passes through the membrane as a filtrate or permeate whereas the remaining portion (the retentate) is recirculated back across the membrane or diverted for other uses. TFF filters include microfiltration, ultrafiltration, nanofiltration and reverse osmosis filter systems. The cross-flow filter may comprise multiple filter sheets (filtration membranes) in a stacked arrangement, e.g., wherein filter sheets alternate with permeate and retentate sheets. The liquid to be filtered flows across the filter sheets, and solids or high-molecular-weight species of diameter larger than the filter sheet's pore size(s), are retained and enter the retentate flow, whereas the liquid along with any permeate species diffuse through the filter sheet and enter the permeate flow. The TFF filter sheets, including the retentate and permeate sheets, may be formed of any suitable materials of construction, including, for example, polymers, such as polypropylene, polyethylene, polysulfone, polyethersulfone, polyetherimide, polyimide, polyvinylchloride, polyester, etc.; nylon, silicone, urethane, regenerated cellulose, polycarbonate, cellulose acetate, cellulose triacetate, cellulose nitrate, mixed esters of cellulose, etc.; ceramics, e.g., oxides of silicon, zirconium, and/or aluminum; metals such as stainless steel; polymeric fluorocarbons such as polytetrafluoroethylene; and compatible alloys, mixtures and composites of such materials. Cross-flow filter modules and cross-flow filter cassettes useful for such filtration are commercially available from SmartFlow Technologies, Inc. (Apex, N.C.). Suitable cross-flow filter modules and cassettes of such types are variously described in the following United States patents: U.S. Pat. Nos. 4,867,876; 4,882,050; 5,034,124; 5,034,124; 5,049, 268; 5,232,589; 5,342,517; 5,593,580; and U.S. Pat. No. 5,868,930; the disclosures of all of which are hereby incorporated herein by reference in their respective entireties.

In some embodiments, the separator is a reverse osmosis (RO) type separator. Examples of RO type separators include RO spiral membranes available from Koch Membrane Systems (Wilmington, MA) or Synder Filtration (Vacaville, CA).

Saccharification and Fermentation Conditions

The saccharification reaction can be performed at or near the temperature and pH optimum for the catalyst used. In some embodiments of the present methods, the temperature optimum for saccharification ranges from about 15 to about 100° C. In other embodiments, the temperature range is about 20 to 80° C., about 35 to 65° C., about 40 to 60° C., about 45 to 55° C., or about 45 to 50° C. The pH optimum for the saccharification enzymes can range from about 2.0 to 11.0, about 4.0 to 6.0, about 4.0 to 5.5, about 4.5 to 5.5, or about 5.0 to 5.5, depending on the enzyme.

The amount of catalyst added to the reaction can be adjusted based on the cellulose content of the biomass and/or the amount of solids present in a composition comprising the biomass, and also on the desired rate of cellulose conversion. For example, in some embodiments, the amount of enzymes added is based on % by weight of cellulose present in the biomass, as specified by the enzyme provider (s). The % of enzyme added by weight of cellulose in such embodiments can range from about 0.1% to about 20% on this basis.

Non-limiting embodiments will now be described.

DESCRIPTION OF EMBODIMENTS

Turning now to FIG. 1, one illustrative embodiment will be described. As shown in FIG. 1, biomass (BM) plus saccharification enzymes (E) and water are added to a high-shear milling/saccharification unit. The BM is treated for 4-6 hours, and the partially saccharified biomass mixture is passed through a solid-liquid separation (SLS) unit. The SLS separates the mixture into a liquid stream comprising sugars that is sent to a sugar reservoir. In this and other embodiments described herein, the sugar can be converted to biofuels, biochemicals, chemicals, or other downstream products as desired.

The solids stream with associated enzymes (SE) is passed back to the high-shear milling/saccharification unit, and incubated for an additional 6-8 hours. The hydrolyzed biomass can then be passed through the SLS to recover a liquid stream with additional sugars.

In a variation of this embodiment, the BM+E is added to a high-shear milling/saccharification unit. The BM is treated for 4-6 hours, and the partially saccharified biomass mixture is passed through a solid-liquid separation (SLS) unit. The liquid stream is processed as above, and the solid stream is added back to the high-shear milling/saccharification unit without additional biomass. The solids are further saccharified for an additional 12 hours, and are then passed through the SLS device to produce a second liquid stream comprising sugars and a second solids stream that is purged, or used for a downstream product.

Figure 2:
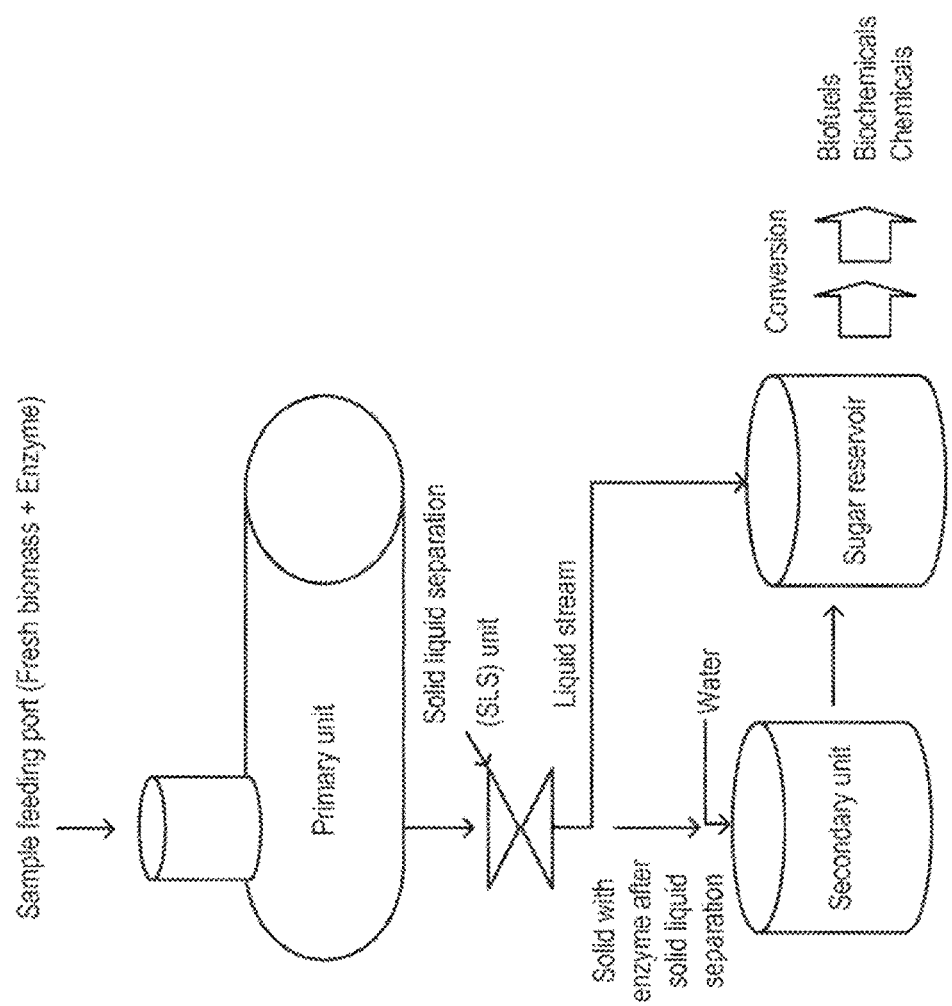
FIG. 2 shows another illustrative embodiment of the method described herein.

Turning now to FIG. 2, another illustrative embodiment will be described. As shown in FIG. 2, biomass (BM) plus saccharification enzymes (E) and water are added to a primary high-shear milling/saccharification unit. The BM is treated for 4-6 hours, and the partially saccharified biomass mixture is passed through a solid-liquid separation (SLS) unit to generate a first solids stream and a first liquid stream. In this embodiment, the first solids stream is added to a secondary high-shear milling/saccharification unit. The first solids are incubated for an additional 6-8 hours under conditions suitable to generate additional sugars. These hydrolyzed solids are then passed through the SLS to generate a second solids stream and a second liquid stream, and the second liquid stream with the additional sugars is added to the sugar reservoir, as above. The second solid stream is purged, or used for a downstream product.

In a variation of this embodiment, the partially saccharified biomass is separated using a first SLS to produce a first liquid stream comprising sugars and a first solids stream with associated enzymes (SE). The first solids are added to a secondary unit, which in one embodiment is a high-shear milling/saccharification unit (with water added as necessary to dilute the solids into a shiny), and incubated for an additional 12 hours to generate hydrolyzed solids. The hydrolyzed solids mixture is separated using a second SLS to produce a second liquid stream (L) with sugars and a second solids stream (S). The sugars from both the first liquid stream and the second liquid steam can be processed as described herein, for example, converted to biofuels, biochemicals, chemicals, or other downstream products as desired. The second solids stream can be purged, or used for a downstream product.

Figure 3:
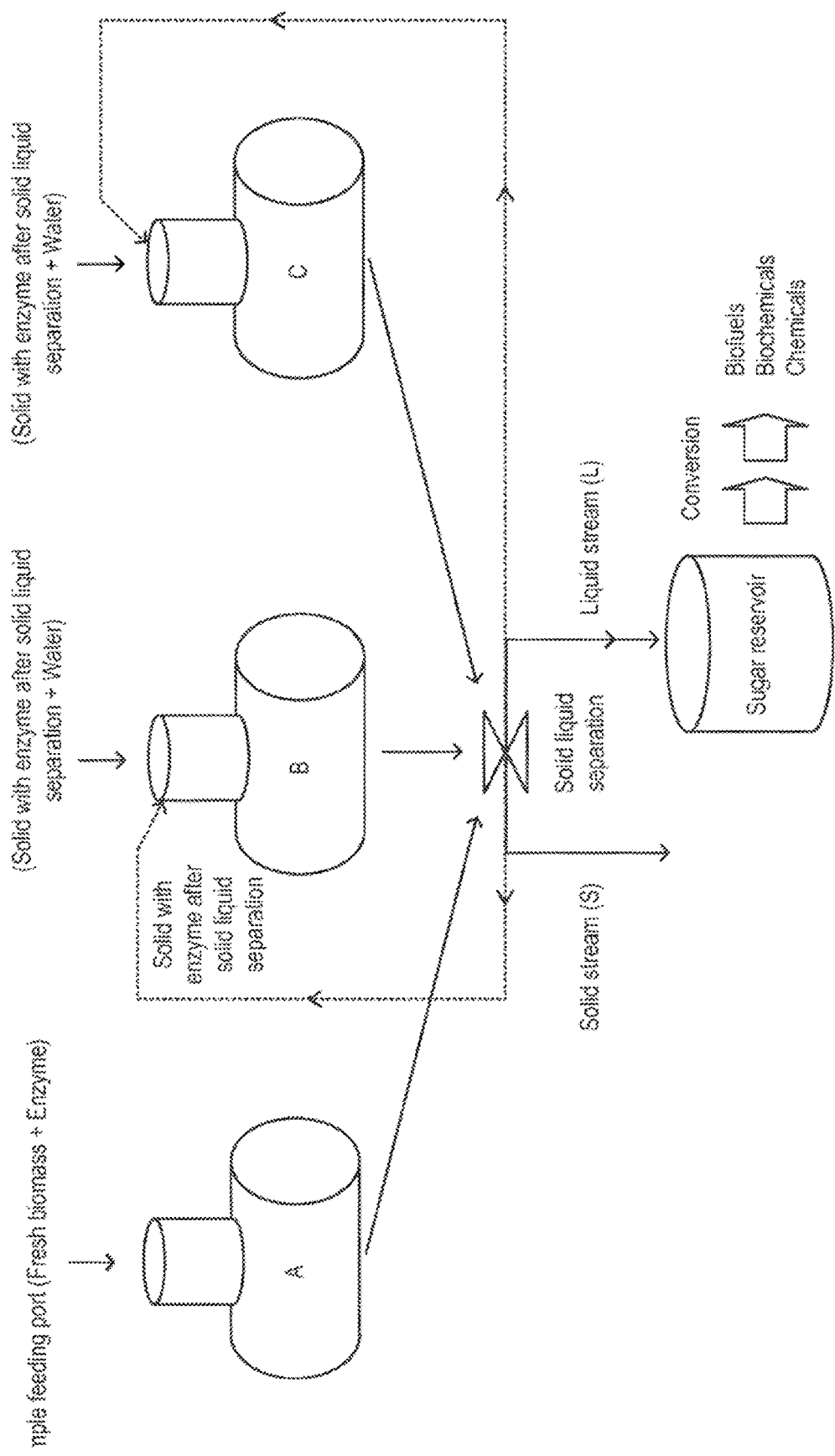
FIG. 3 shows a third illustrative embodiment of the method described herein.

Turning now to FIG. 3, another illustrative embodiment will be described. As shown in FIG. 3, biomass (BM) plus saccharification enzymes (E) and water are added to a primary high-shear milling/saccharification unit (A). The BM is treated for 4-6 hours, and the partially saccharified biomass mixture is passed through a solid-liquid separation (SLS) unit to produce a first liquid stream (L) comprising sugars and a first solids stream (S) with associated enzymes (solid with enzyme). In this embodiment, the solid stream can be added to a second tank (B), which in some embodiments is a high-shear milling/saccharification unit. The solids added to unit (B) are incubated for an additional 6-8 hours under conditions suitable to generate additional sugars and a hydrolyzed solids stream. The hydrolyzed solids stream is then passed through the SLS to generate a second liquid stream and a second solids stream, and the second liquid stream with the additional sugars is added to the sugar reservoir, as above. The second solids stream with enzymes can be added to a third tank (C), with water as necessary to dilute the solids to form a slurry. In some embodiments, the third tank (C) is a high-shear milling/saccharification unit. The second solids are incubated in the third unit (C) for an additional 8-12 hours under conditions suitable to generate additional sugars. The second hydrolyzed solids are then passed through the SLS to generate a third solids stream and a third liquid stream, and the third liquid stream with the additional sugars is added to the sugar reservoir, and the remaining solids can be purged or used for downstream products or recycled back to the units A, B, or C. It will be understood that, whereas only one SLS unit is shown, more than one SLS unit can be used, for example, an SLS device can be located between each saccharification unit to separate the hydrolyzed solid mixture into a solid stream and a liquid stream. In some embodiments, each SLS device is the same type of device (e.g., a membrane filter device), whereas in other embodiments the SLS devices are different from each other (e.g., a centrifuge and a TFF device).

Figure 4:
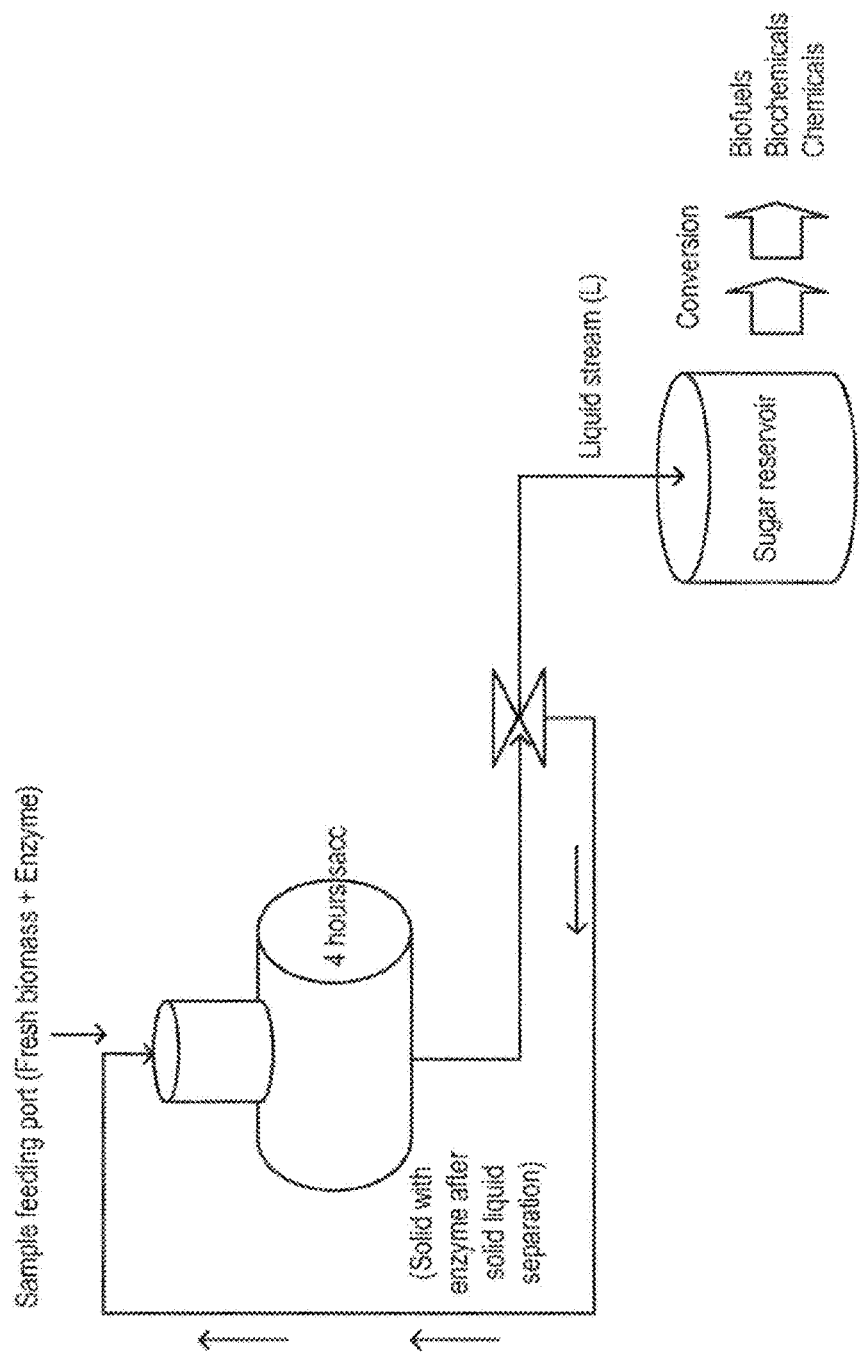
FIG. 4 shows a fourth illustrative embodiment of the method described herein.

Turning now to FIG. 4, an illustrative embodiment of a continuous batch process for treating biomass will be described. As shown in FIG. 4, biomass (BM) plus saccharification enzymes (E) and water as necessary are added to a high-shear milling/saccharification unit. The BM is treated for 4 hours under conditions suitable to hydrolyze components of the biomass to sugars, and the partially saccharified biomass mixture is passed through a solid-liquid separation (SLS) unit to produce a liquid stream (L) comprising sugars and a solids stream with associated enzymes (solid with enzymes). The liquid stream is added to the sugar reservoir. The solids with enzymes stream is added back to the saccharification unit, and combined with fresh biomass and additional enzyme, as necessary to ensure efficient hydrolysis. The solids/biomass/enzyme mixture is again treated for 4 hours under conditions suitable to hydrolyze components of the biomass to sugars. The process is repeated, such that after each separation step, the solids with enzymes are combined with fresh biomass in the saccharification unit under conditions suitable to hydrolyze components of the biomass to sugars. However, because the enzymes in the solids stream are recycled and contacted with the fresh biomass, less additional enzyme needs to be added at each round. The process described above therefore reduces the amount of enzymes required to hydrolyze fresh biomass, which reduces the operating costs of the biofuel facility.

In another aspect, the invention provides a system for treating biomass. In one embodiment, the system comprises: a first auger, the first auger comprising: a solids inlet, a screw inside the auger to direct a solid mass in the auger from a first end to a second end, a liquid outlet at the first end, and a solids outlet at the second end; a separator suitable for separating the biomass into a liquid phase and a solids phase and positioned between (i) the liquid outlet and (ii) the screw and the solids outlet; and a second auger comprising: an inlet in fluid communication with the solids outlet for receiving a solids mass from the first auger; and a solids outlet.

In some embodiments, the system further comprises a second separator suitable for separating the biomass into a liquid phase and a solids phase and positioned between (i) the solids outlet of the first auger and (ii) the inlet of the second auger, wherein the second separator is in fluid communication with the solids outlet of the first auger and the inlet of the second auger.

In some embodiments, the first and/or second separator is a screen, a vibrating screen, centrifuge or a press or a combination of these unit operations in series. In some embodiments, the first and/or second separator is in fluid communication with a filter suitable for separating the liquid phase into a filtrate and retentate. In some embodiments, the filter is in fluid communication with the liquid outlet of the first auger and the inlet of the first and/or second auger. In some embodiments, filter unit has a pore size such that the retentate contains concentrated enzymes and/or polymer additives such as polyethylene glycol (PEG) when compared to the filtrate or permeate.

In some embodiments, the screw transports the solids mass in a direction opposite that of liquid flow inside the auger. In some embodiments, the auger is inclined such that the liquid outlet is lower than the solids outlet.

In some embodiments, the first and/or second auger further comprises additional inlets for adding biomass, solids, enzymes, and/or recycle streams.

In some embodiments, the first auger does not have a liquid outlet and all the material is conveyed via the screw to the second auger.

In some embodiments, the system further comprises at least one additional auger comprising: an inlet in fluid communication with the solids outlet of the first and/or second auger; and a solids outlet; wherein the at least one additional auger is aligned in series with the first and second augers such that a solid mass is directed through the series. In some embodiments, the solids outlet of at least one of the augers is in fluid communication with a third separator suitable for removing liquids from the treated biomass.

In some embodiments, the residence time in the first auger can be sufficient to hydrolyze about 10% to 20% to 30% to 40% of the biomass. The residence time in first auger can be from 0.5 to 36 hours, preferably 1 to 4 hours. The residence time in the second and subsequent augers can be 0.25 to 4 hours.

EXAMPLES

Example 1

This example shows an increase of saccharification efficiency of pretreated biomass after separation of solid and liquid phases.

Thermally pretreated biomass (30 gallon scale) was saccharified under the following conditions: Cellulases (Accellerase Trio) were added to the pretreated biomass, followed by mixing, and samples were taken taken at T=0, 12, 24 and 48 hours, post enzyme addition.

The biomass samples taken at T=0, 12, 24 and 48 hours, post enzyme addition were centrifuged and solid residues were separated from the liquid. The solid residues were re-suspended with fresh water and processed for further saccharification by incubation of the slurry for 24 hours. The samples were then analyzed for glucose and xylose content via High Performance Liquid Chromatography (HPLC) using methods well known in the field. The sugar production was recorded in % (w/v) and the conversion calculated on the basis of total cellulose and hemicellulose in the biomass.

In some cases, both liquid and solid portions were supplemented with solka floc (SF) biomass to observe the further hydrolysis of SF in both portions. The rationale of SF addition to the liquid and solid portions is to (i) understand the localization and functional attributes of active cellulases in the solid residues or in the liquid; and (ii) provide evidence that the new biomass addition to the solid residues and or liquid will be hydrolysed without addition of any additional enzyme cocktail. Therefore, here, solka floc represents a fresh cellulosic biomass which also contains xylan. Solka floc is a standard cellulose-containing biomass for testing cellulosic enzyme activity. It is a simpler biomass compared to the lignocellulosic biomass and less homogenous preparation of cellulose compared to Avicel. Solka floc hydrolysis offers an advantage of measuring glucan and xylan conversion by tracking glucose and xylose release during saccharification.

Sampling was performed at: T=0, T=24 hr. Saccharification was performed at 50° C. under standard conditions. Laboratory scale saccharification was done in 100 g of material in 500 mL flasks. A general saccharification process herein mentioned throughout the text is as follows: Thermally pretreated biomass was pH adjusted to 5 using aqueous ammonium hydroxide. The material was then contacted with Accelerase Trio. The addition of enzyme was ensured by calculating the concentration of Accelerase Trio needed on the basis of the glucan content, amount of biomass and solid % of the biomass in the reaction. The well mixed biomass was transferred to 500 mL flasks (100 gm each) in triplicates for the saccharification.

Figure 5:
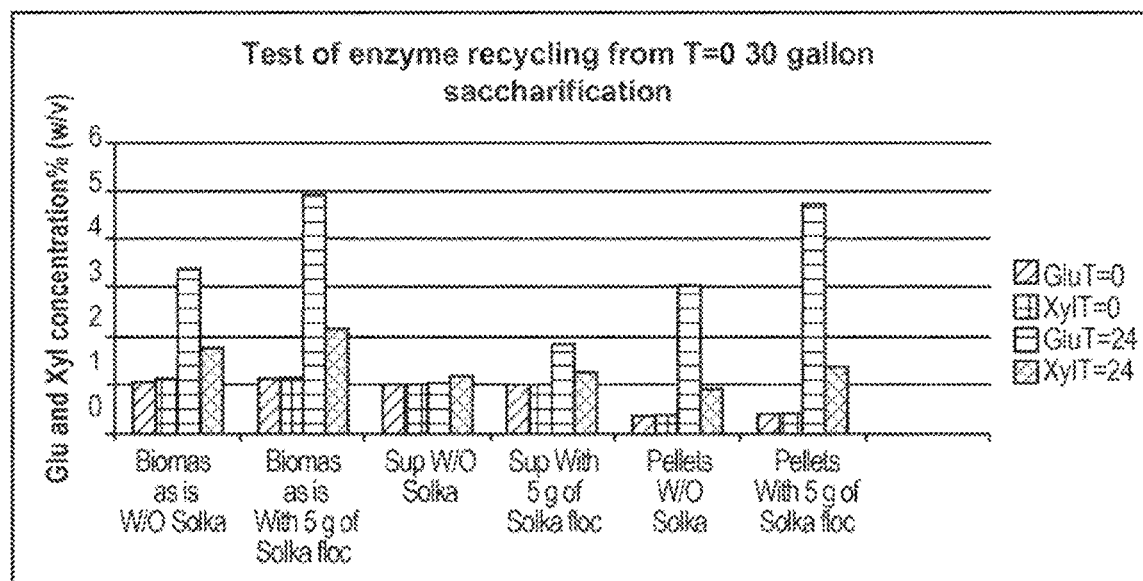
FIG. 5 shows the results of a shake flask scale saccharification test using thermally pretreated, but not milled, biomass. The biomass is contacted with enzyme in a 30 gallon reactor and mixed to ensure homogeneity. A biomass aliquot is immediately withdrawn (T=0) and centrifuged to produce a solid pellet and a liquid supernatant (Sup). Solka Floc (SF), a calibrated source of cellulose and hemicellulose, is added to both pellet and supernatant, the pellet diluted, and the saccharification allowed to continue for 24 hours.

The biomass collected from the T=0 of saccharification from the 30 gallon tank had 3.4% w/v glucose release in 24 hrs ("As Is" with no solka floc and no solid liquid separation). Parallel samples containing solka floc as a test substrate for cellulase activity increased glucose release to 4.9% w/v during the same saccharification time (FIG. 5). This was a 44.1% increase in glucose release.

After solid/liquid separation of the same biomass, glucose release was observed in separated saccharified supernatant (Sup) and the solids fraction (Pellets) re-suspended in fresh water. Glucose and xylose levels did not change in 24 hours of saccharification in the Sup phase indicating that the Sup does not contain any available polysaccharides for further saccharification. After 24 hours, the Sup without solka floc had 1.05% w/v glucose which increased to 1.87% in samples containing solka floc. The change in glucose after solka floc addition indicated that the Sup contains cellulases which can hydrolyze the solka floc into glucose monomers.

The solid residue "pellets" without addition of solka floc produced a much higher 3.09% w/v glucose at T24 saccharification, compared to 0.38% at T=0. This demonstrates that the solid residues contain high level of active cellulases which continued to saccharify the biomass even after the separation of the Sup from the solid residues. The solids fraction containing solka floc showed further release of glucose from 0.41% at T=0 to 4.76% at 24 hours (FIG. 5), demonstrating solids-associated cellulase activity on exogenous solka-floc substrate.

These results demonstrate that active cellulases are associated with the solids fraction that show higher activity than the unfractionated "As Is" sample (1.7-fold increase in glucose release, calculated from data presented in FIG. 5).

The biomass "As Is" collected at T=12 of the saccharification had 3.32% w/v glucose which increased little to 3.6% after 24 hrs saccharification. This indicated loss of cellulase productivity in the "As Is" sample, compared to the T=0 sample. This was corroborated by the lower C6 conversion in samples containing solka-floc: 4.6% w/v glucose at 24 hrs sacc in samples containing solka floc from base of 3.6% w/v glucose in samples lacking solka floc. Thus, the activity of enzymes on exogenously added substrate was lower than at the T=0 sampling point, which may result from glucose end-product inhibition of C6 cellulases, inaccessible substrate or other factors.

Figure 6:
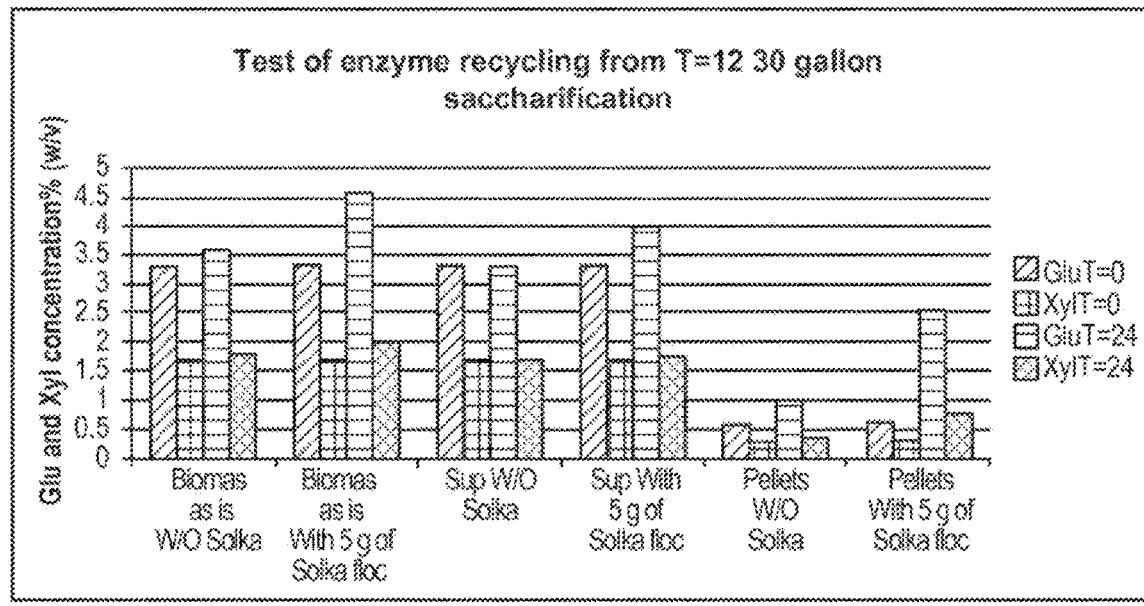
FIG. 6 shows the results of a shake flask scale saccharification test using thermally pretreated, but not milled, biomass. The biomass is contacted with enzyme in a 30 gallon reactor and mixed to ensure homogeneity. A biomass aliquot is withdrawn after 12 hours (T=12) and centrifuged to produce a solid pellet and a liquid supernatant (Sup). Solka Floc (SF), a calibrated source of cellulose and hemicellulose, is added to both pellet and supernatant, the pellet diluted, and the saccharification allowed to continue for an additional 24 hours.

Consistent with observations from the T=0 sample in FIG. 5, the Sup from the T=12 time point (FIG. 6) had increased glucose upon addition of solka floc, from 3.32% to 3.99% (FIG. 6), indicating that the Sup contains active cellulases. The solids fraction showed higher relative glucose increase in which samples without solka floc increased from 0.61% w/v to 1.0%, and with solka floc increased 0.6 to 2.5% after 24 hrs saccharification (FIG. 6).

Figure 7:
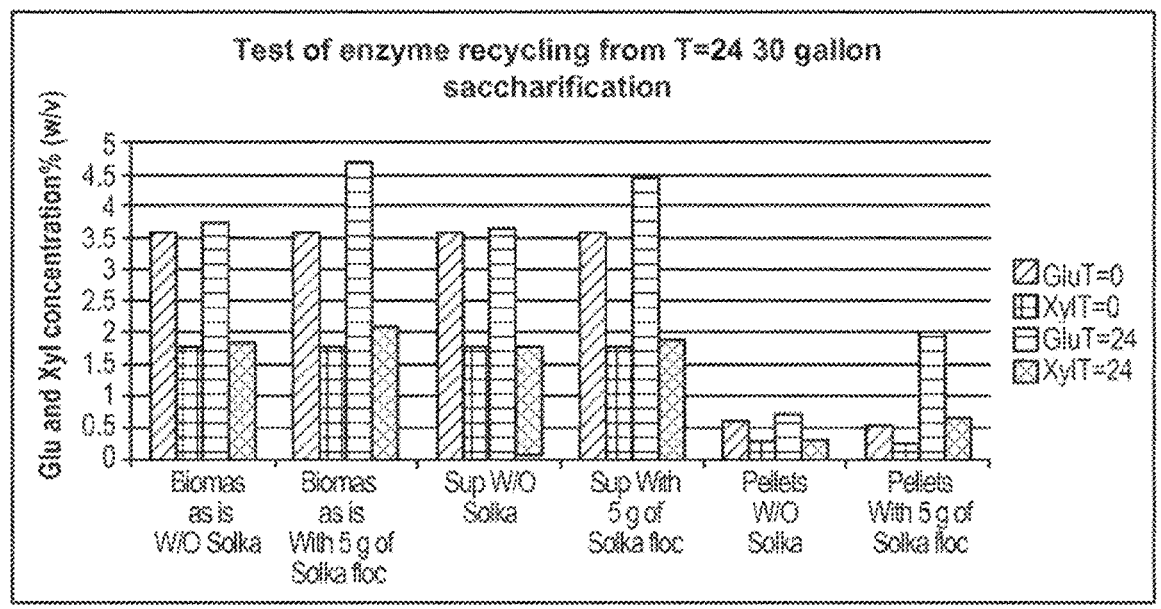
FIG. 7 shows the results of a shake flask scale saccharification test using thermally pretreated, but not milled, biomass. The biomass is contacted with enzyme in a 30 gallon reactor and mixed to ensure homogeneity. A biomass aliquot is withdrawn after 24 hours (T=24) and centrifuged to produce a solid pellet and a liquid supernatant (Sup). Solka Floc (SF), a calibrated source of cellulose and hemicellulose, is added to both pellet and supernatant, the pellet diluted, and the saccharification allowed to continue for an additional 24 hours.

FIG. 7 shows the enzyme recycling tests results obtained from the 24 hours saccharified material from 30 gallon tank. In the control saccharification, "As Is" biomass without solka floc had little increase in glucose release when incubated further 24 hours. When solka floc was added, the glucose increased from 3.6 to 4.7% (FIG. 7), suggesting that the enzymes are still very active and similar to observations in FIG. 6.

At this time point, glucose release was found to be nearly saturated with the Sup having increased sugar concentration (24 hours saccharified material of 30 gal sample). The solids fraction incubated with solka floc still showed an increase in glucose release, but less than the 12 hr. sample. It indicated that the solid residues have the active cellulases, however the 24 hours saccharification of the biomass has less accessible polysaccharides in it (FIG. 7).

Figure 8:
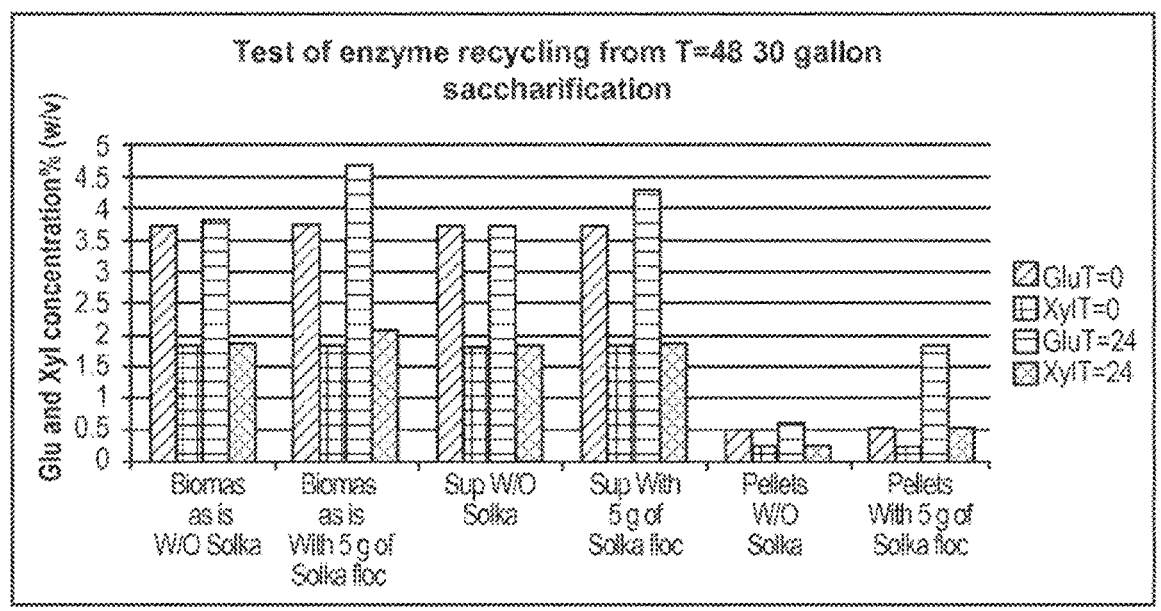
FIG. 8 shows the results of a shake flask scale saccharification test using thermally pretreated, but not milled, biomass. The biomass is contacted with enzyme in a 30 gallon reactor and mixed to ensure homogeneity. A biomass aliquot is withdrawn after 48 hours (T=48) and centrifuged to produce a solid pellet and a liquid supernatant (Sup). Solka Floc (SF), a calibrated source of cellulose and hemicellulose, is added to both pellet and supernatant, the pellet diluted, and the saccharification allowed to continue for an additional 24 hours. of SLS of 48 hours saccharified material from (T=48 material) from 30 gallon saccharification and continuous saccharification.

The results were similar with the 48 hours saccharified materials (FIG. 8) showing similar glucose levels before and after 24 hrs. saccharification, and in the absence and presence of solka floc.

These results indicate that functional cellulases are in the solids fraction and remain active through 48 hours for recycling.

Example 2

Effects of early-stage solid-liquid separation on saccharification and fermentation.

Figure 9:
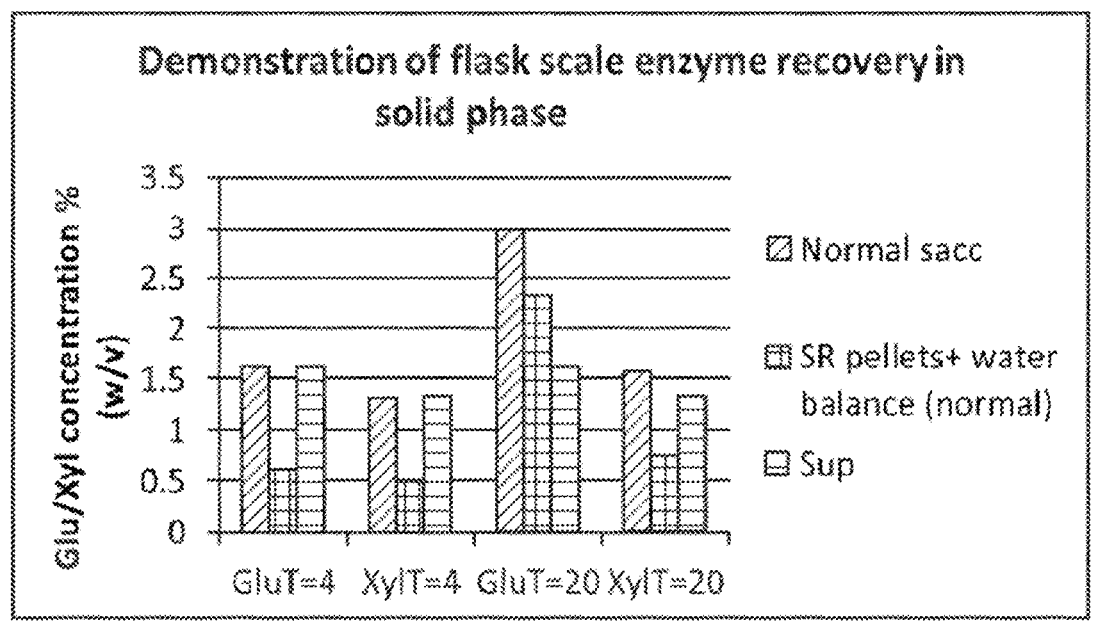
FIG. 9 shows glucose and xylose concentrations resulting from shake flask testing in which thermally pretreated, but not milled, biomass is contacted with enzyme, mixed, and allowed to react for 4 hours. The biomass was then centrifuged, the pellet resuspended with an equivalent volume of water, and the diluted pellet and supernatant allowed to continue reacting with residual enzyme for an additional 20 hours. Sugar concentration were measured at T=4 and T=20 hours respectively. The control sample, which was not centrifuged, is labeled as Normal Sacc.

The efficiency and reproducibility of continuous saccharification and fermentation was determined after removing Sup from the saccharified biomass at an early time point. (SLS was conducted at T=4 hours.) FIG. 9 shows glucose and xylose release from the biomass, compared to centrifuged solid residues and the Sup in T=20 hours (total saccharification). These results indicate that the sugar release was higher when the total solids and Sup glucan conversion percentage were added together (2.34%+1.63%=3.97% w/v glucose), compared to the unfractionated material which gave 3% w/v glucose.

Solids/liquids separation at early time of saccharification, followed by continued saccharification of each fraction produces higher overall sugar yield than from unfractionated material.

Example 3

Fermentation of sugars released by milling saccharification and solid-liquid separation.

Biomass after 4 hours of saccharification was separated into solid and liquid fractions by centrifugation of the saccharified biomass (T=4 saccharified). The liquid stream with the glucose and other sugars were chilled to 4° C., whereas the solid residues were supplemented with an equivalent volume of fresh water and saccharified for an additional 12 hours (total saccharification time was 16 hours). The initial furfural concentration in the biomass was 900 ppm, which is near the upper limit for acceptable fermentation of said yeast strain used in this experiment.

Figure 10:
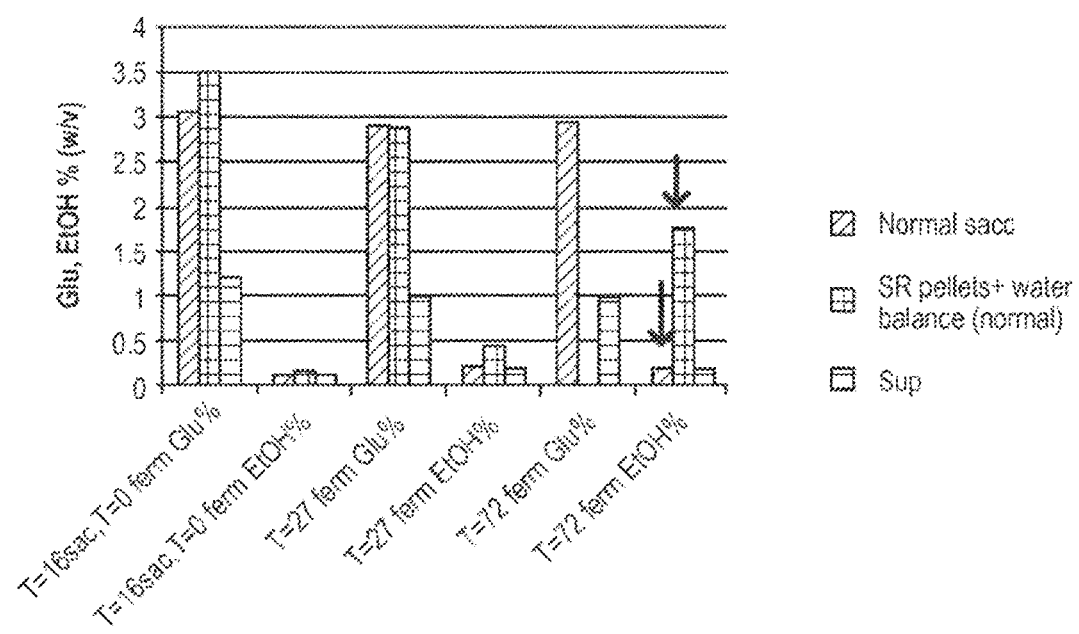
FIG. 10 shows the results of fermentation of post saccharified solids/liquids fractions using an engineered *Saccharomyces cerevisiae* yeast strain. The solid residues of the saccharified biomass normalized with water demonstrated high glucose to ethanol conversion. Arrows indicate the direct comparison of ethanol production from the normal saccharified biomass and solid residues normalized with water.

Samples from a) 16 hours saccharified biomass, b) 12 hours saccharified solid residues (total saccharification time was 16 hours) and c) Sup separated at T=4 saccharification, were inoculated with 40×10$^6$ yeast cells/gm of material and fermented (FIG. 10).

Fermentation was unsuccessful for the 16 hr. saccharified biomass and Sup, but was successful for the 12 hr. saccharified solid residues, likely due to of removal of inhibitors from the liquid stream leaving most of the active cellulase mixtures in the solids fraction.

These results, using pretreated biomass with high furfural concentration, demonstrate that separation of the early saccharified material allows sugars derived from the solids fraction to be more efficiently fermented.

Example 4

Continuous saccharification of >30% hydrothermally pretreated biomass with milling saccharification and solid-liquid separation.

Biomass with solid % of >30% was milled and saccharified, and after 4 hours was separated into solid and liquid fractions by centrifugation (T=4). The liquid stream with the glucose and other sugars were chilled to 4° C., whereas the solid residues were supplemented with an equivalent volume of fresh water and saccharified for an additional 16 hours.

Figure 11A:
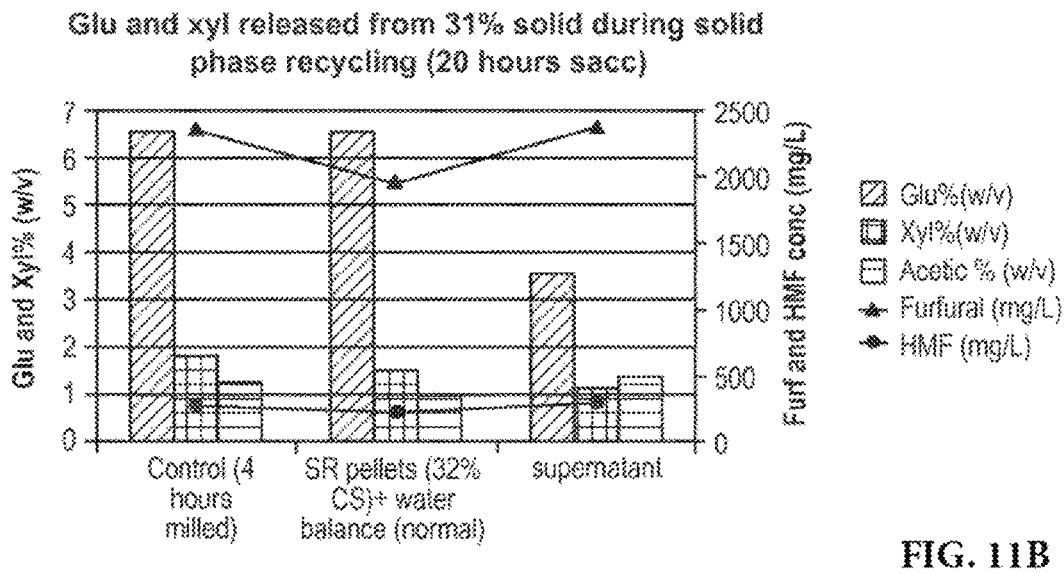
FIGS. 11(A) and (B) show the results of duplicate experiments in which thermally pretreated biomass is saccharified under conditions of high shear agitation using a milling auger. After 4 hours of saccharification, aliquots of biomass are withdrawn and centrifuged. The resulting pellet is diluted with water to the initial concentration of the biomass. Both the diluted biomass pellet and supernatant, as is, are allowed to saccharify for an additional 20 hours in shake flasks without application of additional enzyme. In this FIG., the Control is undisturbed biomass that was allowed to saccharify for the full 24 hours.
Figure 11B:
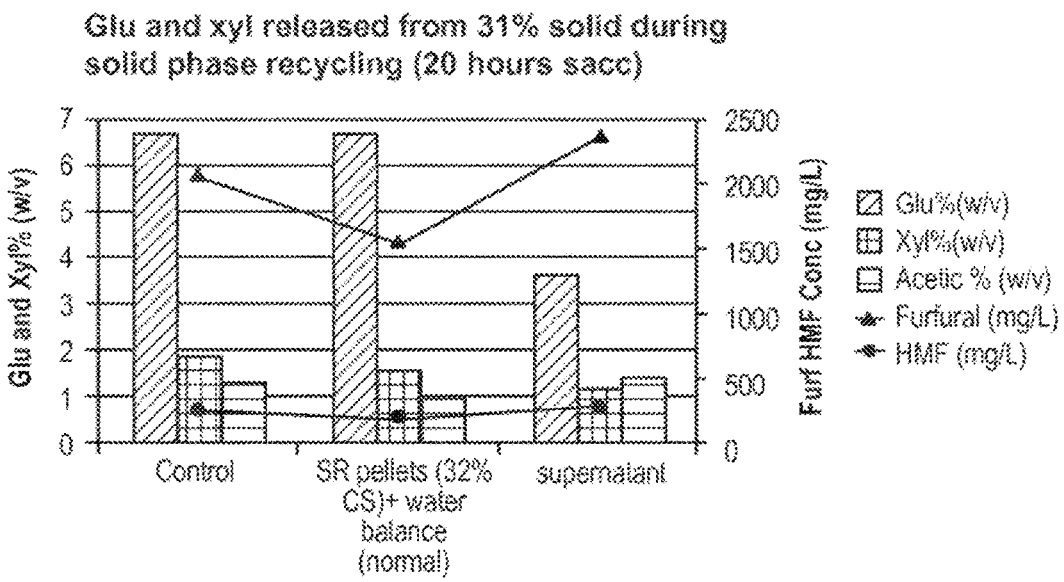

FIG. 11 demonstrates the milling saccharification and solid-liquid separation of high-solid biomass is as efficient as in the lower solids percentage biomass conditions.

The solid phase (water balanced) samples showed the same saccharification efficiency compared to the control suggesting that the simultaneous milling and saccharification in combination of solid phase recycling system works in high solid concentration.

Example 5

Beta-1,4-glycosidic bonds (hence the name, beta-1,4-endoglucanase) link together the beta-D-glucopyranose units of cellulose. Beta-1-4-endoglucanase (EG) enzymes specifically cleave the internal bonds of the cellulose chain. Exoglucanases or cellobiohydrolases (CBH), EG and beta-glucosidases (BG) are needed to completely break down cellulose into glucose monomers. Binding behavior of endoglucanase and beta-glucosidase were determined in hydrothermally pretreated corn stover in order to test their roles for glucan conversion.

Endoglucanase (EG) and beta-glucosidase (BG) (expressed and secreted in a *Saccharomyces cerevisae* strain) were used to test the binding properties of these cellulosic enzymes. EGII has a cellulose binding domain, whereas BG does not.

Figure 12A:
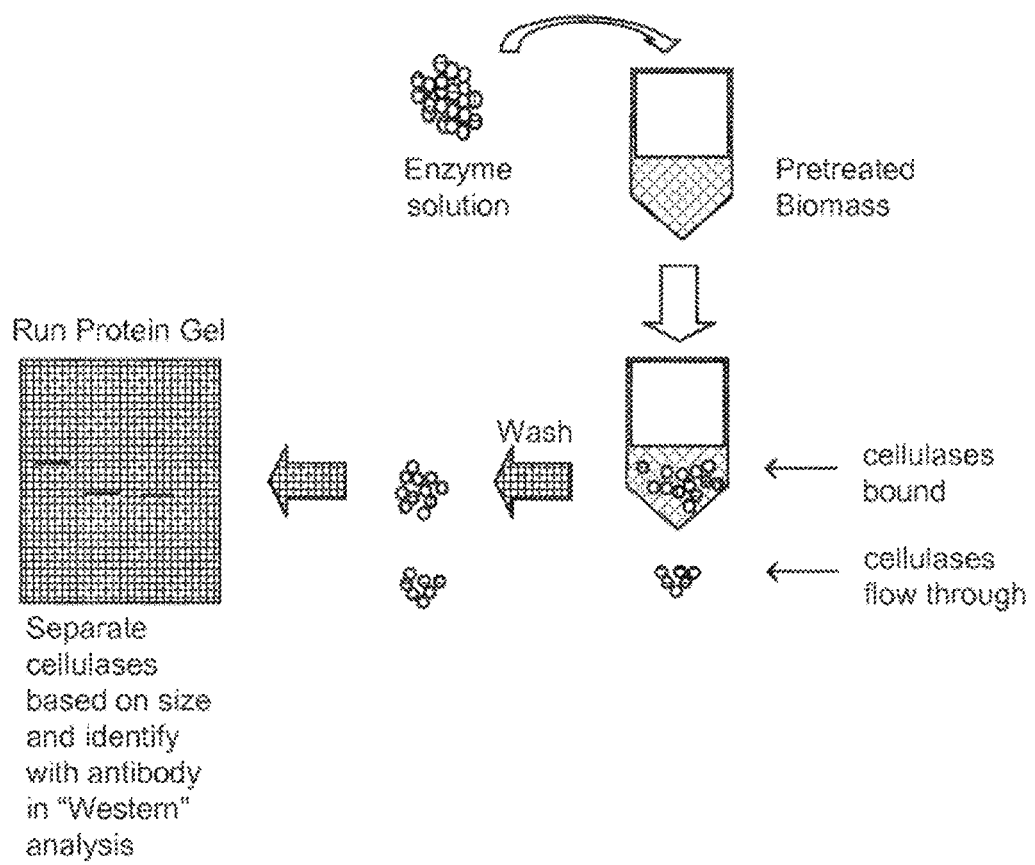
FIG. 12(A) Shows a schematic diagram of a method for detecting cellulases bound to biomass.
Figure 12B:
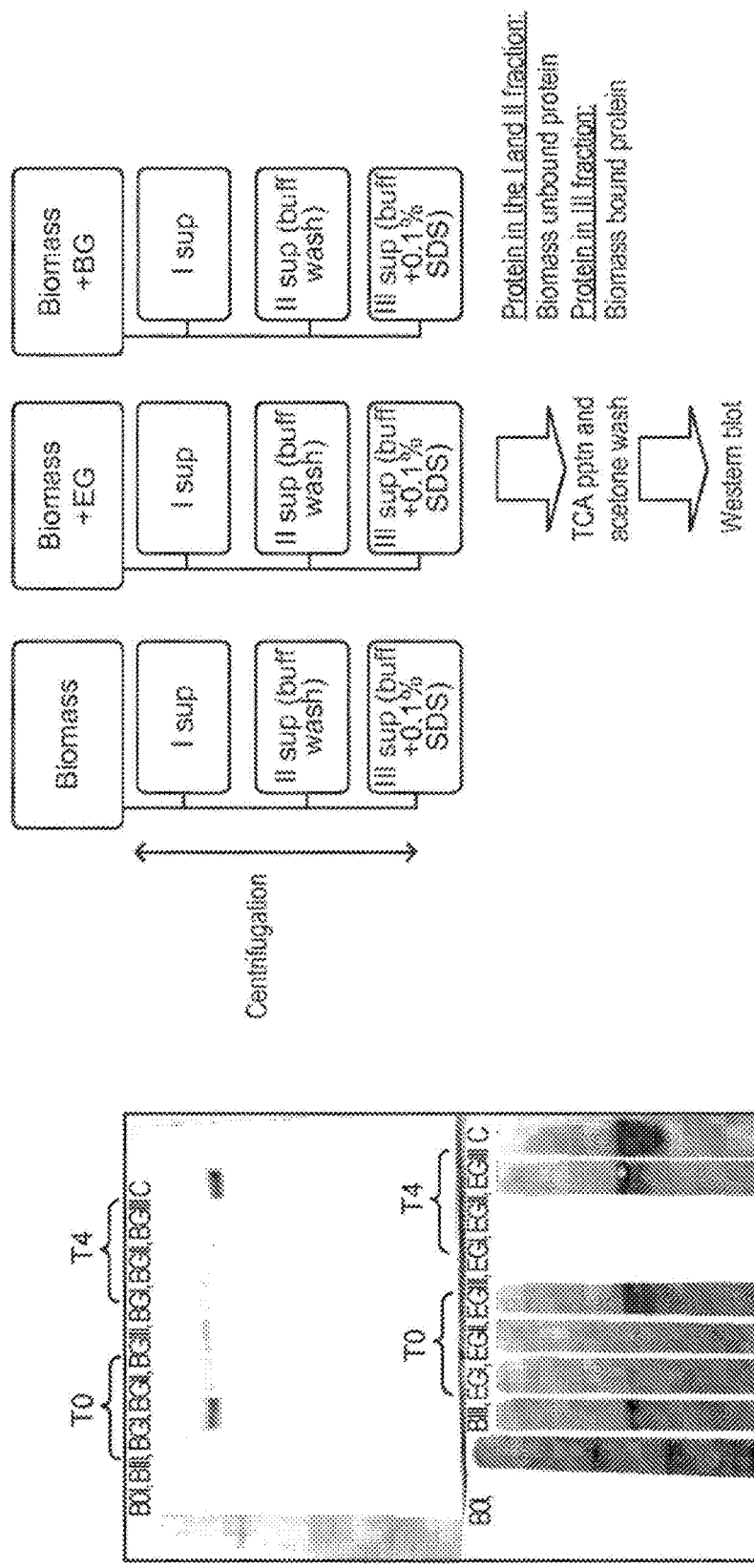
FIG. 12(B) shows Beta-glucosidase (BG) and endoglucanase (EGII) binding properties on pretreated biomass. The right side of the FIG. indicates the work plan for the experiment. BGI, BGII and BGIII indicates: I supernatant (sup), II Sup(buffer wash) and III Sup(buffer+0.1% SDS) (see top right of the FIG.) which is also the same for EGII. T0 and T4 indicate the time point of the sampling (hours).

One gram of hydrothermally pretreated corn stover was mixed with 500 μL (30 μg/μl) of the individually concentrated cellulosic enzyme catalysts and the samples were incubated at 50° C. The supernatants were harvested at different time points with or without buffer washing, in addition to a 0.1% SDS wash. The supernatants were trichloroacetic acid (TCA) precipitated and acetone washed before western blotting using a polyclonal anti-peptide antibody directed towards the individual enzyme catalysts. A schematic diagram is presented in FIG. 12A, and the results of the experiment in FIG. 12B.

Endoglucase (EG) strongly bound the solid phase in contrast to beta-glucosidase (BG) which was visible in the soluble liquid portion of the saccharified material.

Example 6

Beta-glucosidase is a glucosidase enzyme that acts upon β1-4 bonds linking two glucose or glucose-substituted molecules (i.e., the disaccharide, cellobiose). It is an exocellulase with specificity for a variety of beta-D-glycoside substrates. It catalyzes the hydrolysis of terminal non-reducing residues in beta-D-glucosides with release of glucose. Test of beta-glucosidase (BG) behavior in pretreated corn stover was done in order to assess beta-glucosidase localization and activity in early saccharified fractionated biomass.

Biomass was saccharified with cellulosic enzyme cocktail (Accellerase Trio) and incubated for 4 hours. Saccharified biomass was centrifuged and the biomass solids fraction normalized with addition of equivalent fresh water. Saccharification was continued for four hours. Cellobiose (2% w/v) was added to each flask as an exogenous substrate and incubated for 4 hrs. Glucose and xylose were measured by HPLC.

The saccharified biomass harvested in 4 hours and centrifuged to separate solid and liquid fractions. Both the liquid (supernatant) and solid residues were normalized with water, supplemented with 2% cellobiose and incubated at 50° C. in a shaking incubator overnight.

Figure 13:
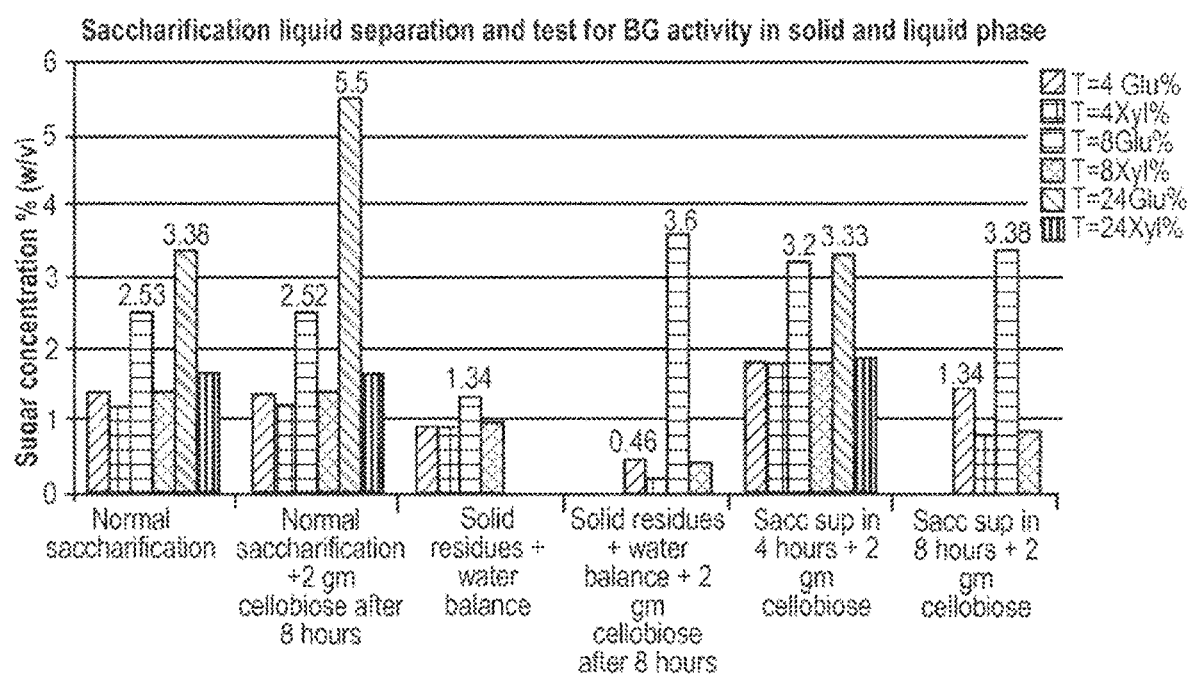
FIG. 13 shows beta-glucosidase (BG) activity in the solid phase and liquid phase after centrifugation following biomass saccharification, demonstrating the concept of enzyme recycle.

FIG. 13 shows the glucose generation in both supernatant and solid fractions (supplemented with cellobiose). BG activity was nearly equally distributed in supernatant and solid residues. Further, two subsequent replacements of liquid from the solid residues still showed the BG activity. BG activity in the supernatant was saturated in 4 hours This example shows the biomass solids fraction retains sufficient BG activity for cellobiose conversion.

Example 7

This example shows that the process described herein can convert 80% of the glucan in corn stover to glucose in 18 hours.

Corn stover with glucan content from 19-40% was used. Hydrothermal pretreatment was done at 140-190° C. for 30-90 mins residence time maintaining the biomass solid % (w/w) ranged between 10-40%. Each experiment was conducted with freshly pretreated biomass. pH adjustment was between 4-6.5 before initiation of saccharification. Saccharification reactions were carried out in the milling reactor. Saccharification temperature was 30 to 60° C. at a rotary speed of 120-200 rpm. A benchtop ball and/or rod milling reactor was filled 20-80% by the biomass (by volume) and a cellulase cocktail was added. Saccharification was conducted using commercial cellulase cocktails (Ctec2 and Htec2; Novozymes, Denmark), 10% (w/w) Ctec2 loading was based on the glucan content of the biomass, whereas 0.5% (w/w) Htec2 was added based on the solid % of the biomass Biomass compositional analysis: Extractives in the biomass were subjected to composition analysis as described by ASTM method 1107. The liquor was evaporated under vacuum and the extractive content was determined gravimetrically. 0.1 g of samples were prepared and characterized by the two-stage acid hydrolysis method described in the Standard Biomass Analytical Procedures (NREL) [TAPPI test method (T22-om 88)]. The first hydrolysis step used 72% sulfuric acid at 30° C. for 1 h. The samples were immediately diluted to 4% and autoclaved for 1 h. The resulting solid residues were reported as acid-insoluble lignin. The sugars in the aqueous phase were quantified via high performance liquid chromatography (HPLC). Glucan, xylan and arabinan contents were quantified by running a standard curve for each sugar species and validated against a standard sugar sample. Acid-soluble lignin was determined by UV absorbance at 205 nm using an extinction coefficient of 110 L/g cm. Ash content was determined by burning the material in an oven at 575° C. and checking for constant weight every 4 h.

Pretreated corn stover was added with the cellulases after the pH adjustment. After thorough mixing of enzyme and biomass, the mixtures were subjected to the mill-saccharification process. SLS were done at T=2 and T=4 hours of milling. In both cases, total saccharification time was 18 hours. Glucan conversion % were recorded before the SLS (T=2 hours, and T=4 hours) and also at 18 hours. Particle size analysis was performed and compared to the T=0 biomass (samples just added with the enzymes before starting the milling-saccharification process) (see Table 1). Glucan conversion rates were calculated for all the test samples.

TABLE 1

| Particle distribution of the materials before and after milling | | | | | | | |
|---|---|---|---|---|---|---|---|
| Volume % | CS T = 0 (1) (μm) | CS Mill Sac T = 2 h (μm) | CS Mill Sac T = 4 h (μm) | CS Mill Sac T = 18 h 2 h SLS (μm) | CS Mill Sac T = 18 h 4 h SLS (μm) | Unmilled T = 18 h (μm) | CS T = 0 (2) (μm) |
| 10 | 26.48 | 11.93 | 6.365 | 2.024 | 1.812 | 29.16 | 29.1 |
| 25 | 56.69 | 27.51 | 15.39 | 5.084 | 4.452 | 115.6 | 64.05 |
| 50 | 131.7 | 64.57 | 32.36 | 12.32 | 10.81 | 323.5 | 145.7 |
| 75 | 305.6 | 153.7 | 65.88 | 26.87 | 23.99 | 693.7 | 332.3 |
| 90 | 637.7 | 364.6 | 126 | 46.47 | 42.38 | 1202 | 674.5 |

Figure 14:
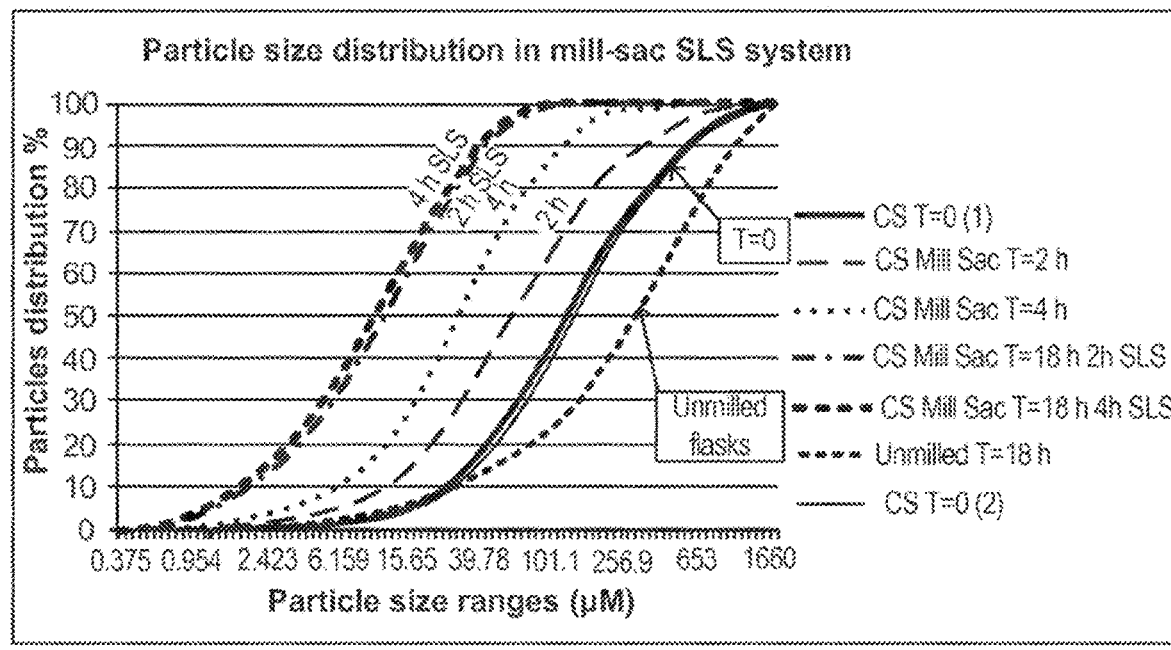
FIG. 14 shows biomass particle size distribution as a function of milling-saccharification and solid liquid separation timing.
Figure 15:
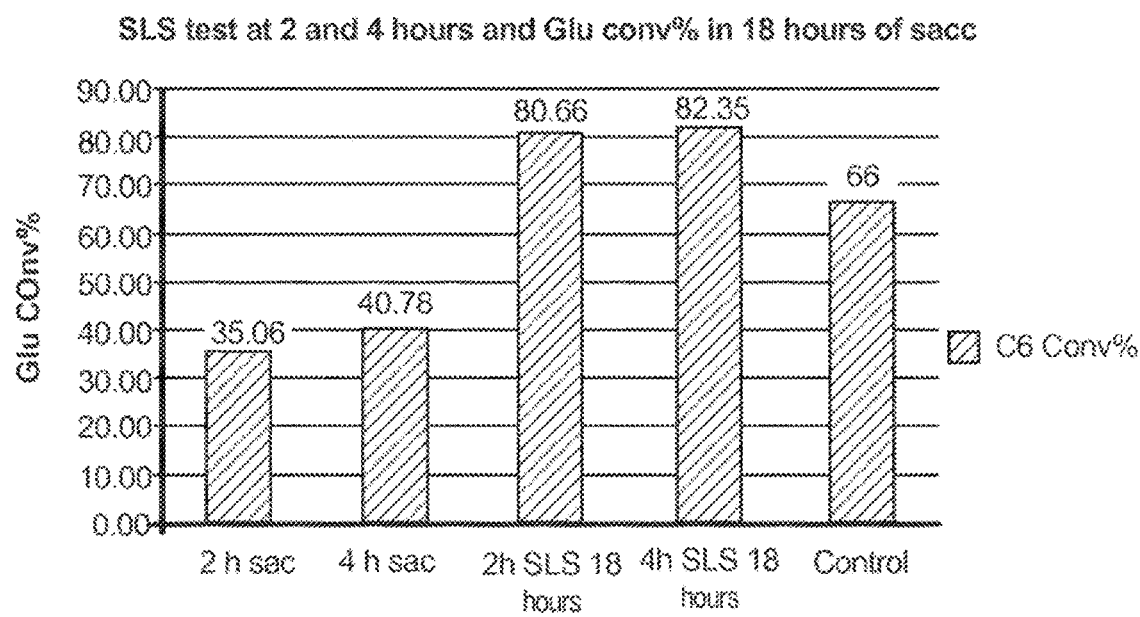
FIG. 15 shows glucan conversion as a function of milling-saccharification and solid liquid separation timing.
Figure 16:
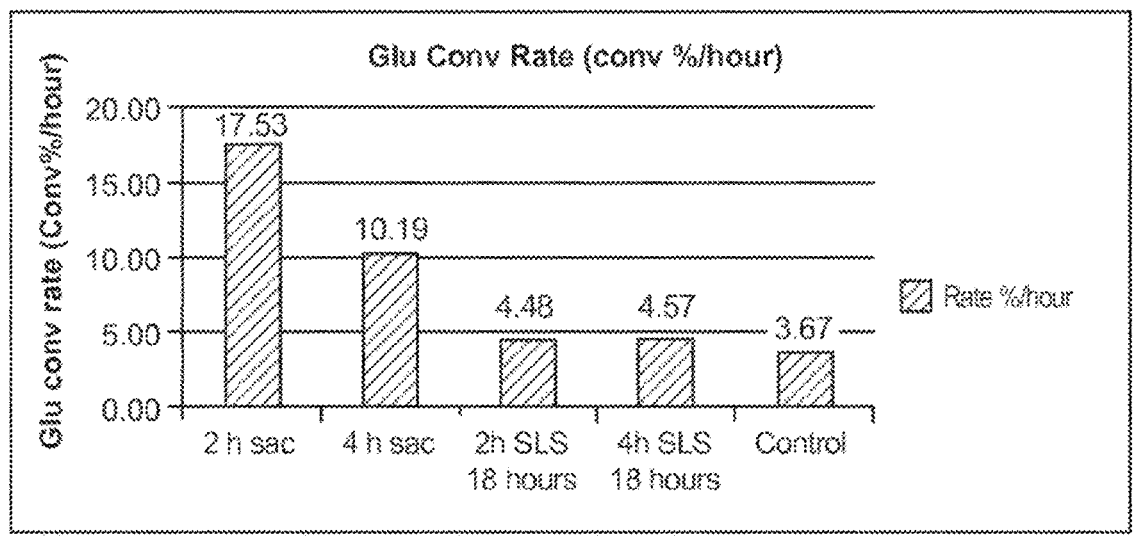
FIG. 16 shows glucan conversion rate (%/hour) as a function of the milling-saccharification and solid liquid separation timing.

FIG. 14 shows the particle size distribution of the material at different time points during milling. FIG. 15 shows the conversion of glucan to glucose (C6) of corn stover treated with the high-shear milling-saccharification in combination with SLS. Saccharification treatment under conditions of high-shear milling for as little as 2 hours, combined with post-separation saccharification treatment of the solid for an additional 16 hours (18 hours saccharification total), resulted in conversion of 80.6% of the glucan to glucose. FIG. 16 shows the glucan conversion rate (%/hour) given in terms of treatment and time.

This example shows that saccharification under conditions of high-shear milling for as little as 2 hours, followed by additional saccharification of 16 hours, resulted in conversion of 80% of the glucan in the biomass to glucose.

Example 8

This example demonstrates 80% glucan conversion in less than 18 hours. The direct correlation of increased glucan conversion with decreased particle size was verified.

In this experiment, SLS was performed after 3 hours with saccharification and particle size distribution analysis performed every three hours until 18 hours.

Figure 17:
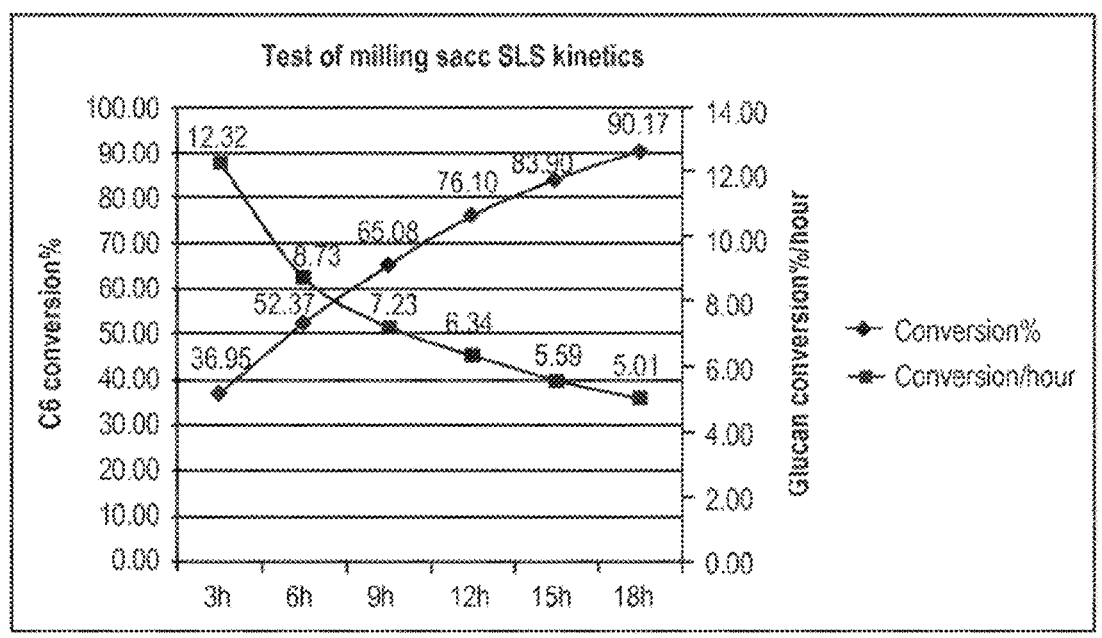
FIG. 17 shows % cellulose conversion to glucose and rates of conversion for biomass hydrolyzed in a bench scale milling device. SLS was conducted following 3 hours of hydrolysis, the solids fraction diluted with water to the original biomass concentration, and hydrolysis allowed to continue without additional enzyme for a total of 18 hours.
Figure 18:
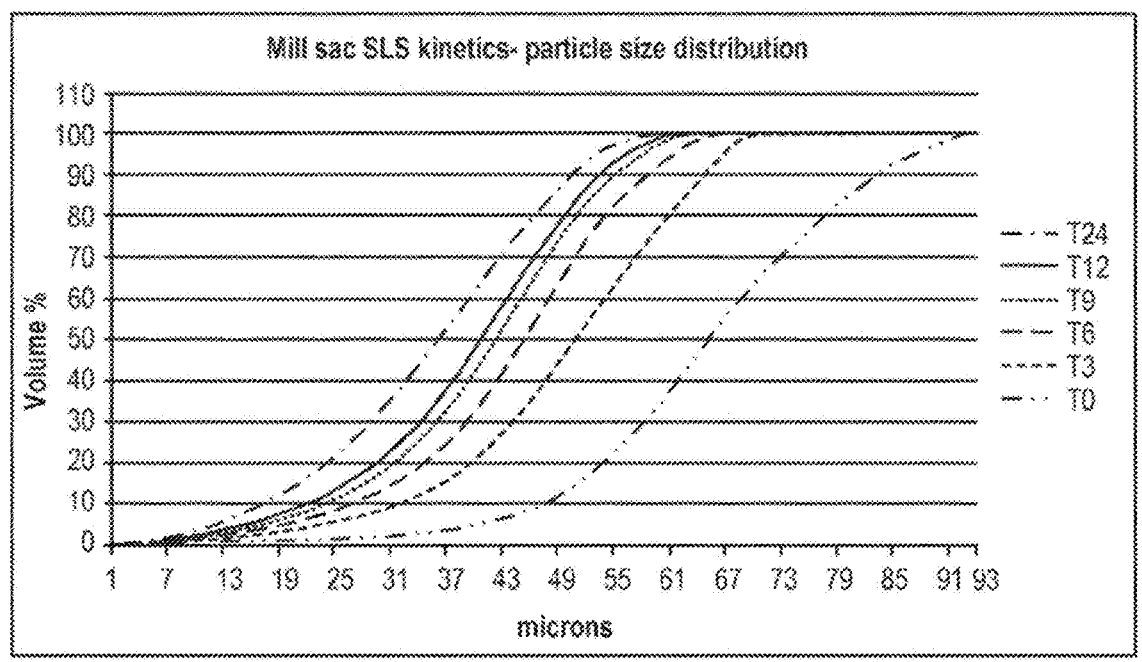
FIG. 18 shows the milling saccharification solid liquid separations kinetics and particle size distribution analysis at T=0 to T=24 hours.

As shown in FIG. 17, the process gave >80% C6 at 15 hours of saccharification time. 18 hours gave >90% C6 conversion. FIG. 18 shows the particle size distribution of the saccharified (T=3 to T=24) and unsaccharified (T=0) material. Linear inverse correlation between particle size and glucan conversion was observed: highest conversion was observed with smaller particle size. At T=24 hour saccharification, the particle size decreased to a range of 1.8 to 40 μm from initial 30 to 800 μm at T=0.

Example 9

This example demonstrates a system for generating sugar from biomass where the enzymes are contacted with biomass under conditions suitable to hydrolyze the biomass into sugars using augers. The enzymes are recycled using a vibrating sieve and tangential flow filtration system (TFF).

In this example, the auger liquid phase was separated from the auger solid phase using a screen at the bottom of the auger. This auger's liquid phase was further separated using a vibrating screen to generate a first phase and a first solids phase. The first liquid phase was stored under conditions suitable to produce sugars. In a second step, the first liquid was separated using a TFF membrane into a second liquid phase or permeate containing sugar and some dissolved solids and a second solids phase or retentate containing enzymes, sugar, and any remaining particulate solids. The retentate was then recombined with the auger solids in each auger by use of counter current washing. The biomass used in this example was bagasse, and the system was operated continuously over 10 days.

Figure 19:
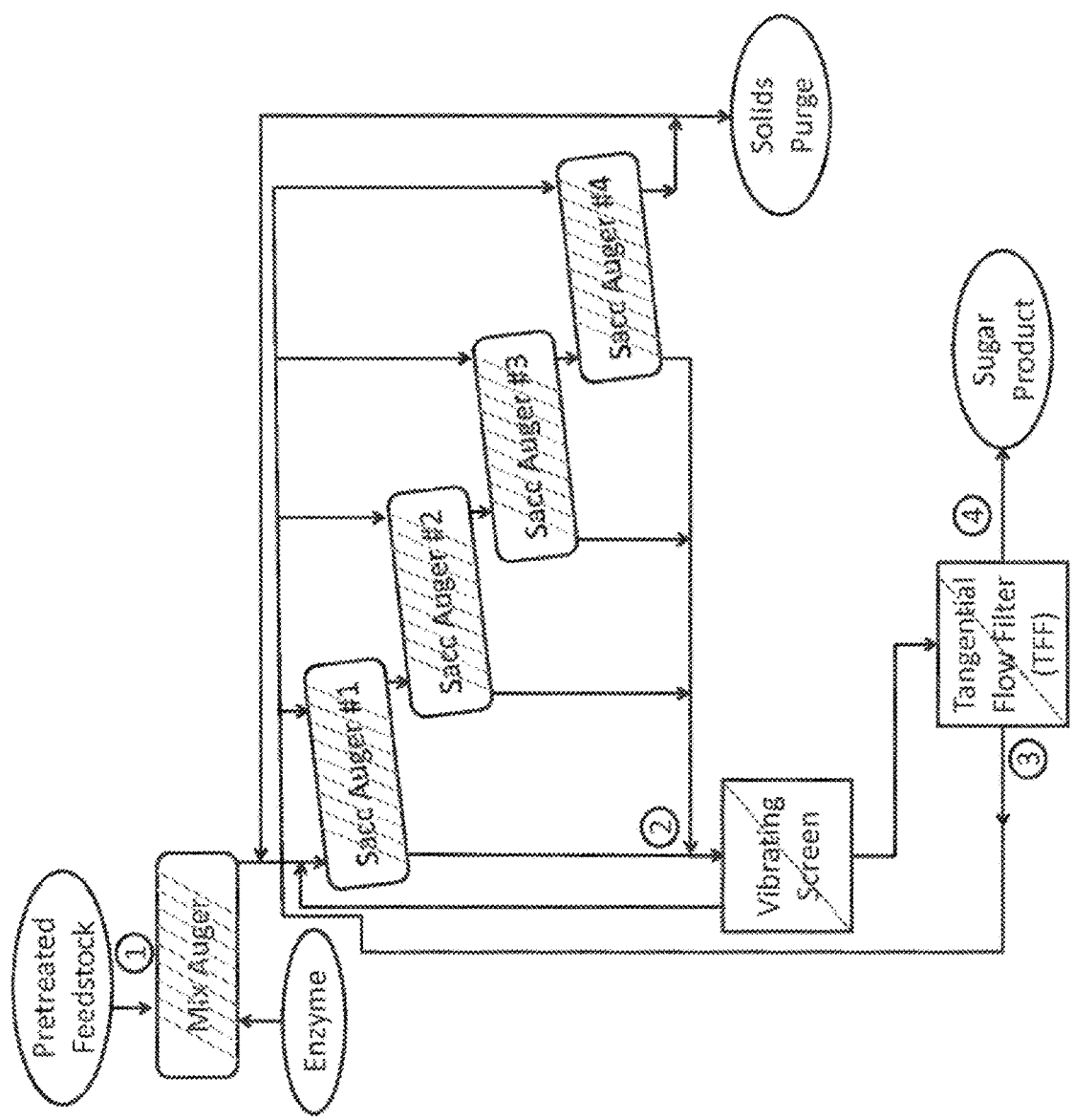
FIG. 19 shows a fifth illustrative embodiment of the method described herein. A continuous process encompassing mixing and saccharification augers, a vibrating screen for separation of solids and liquids, a Tangential Flow Filter (TFF) for separating the liquid stream further into a second solids and second liquids stream, and the presence of recycle loops.
Figure 20:
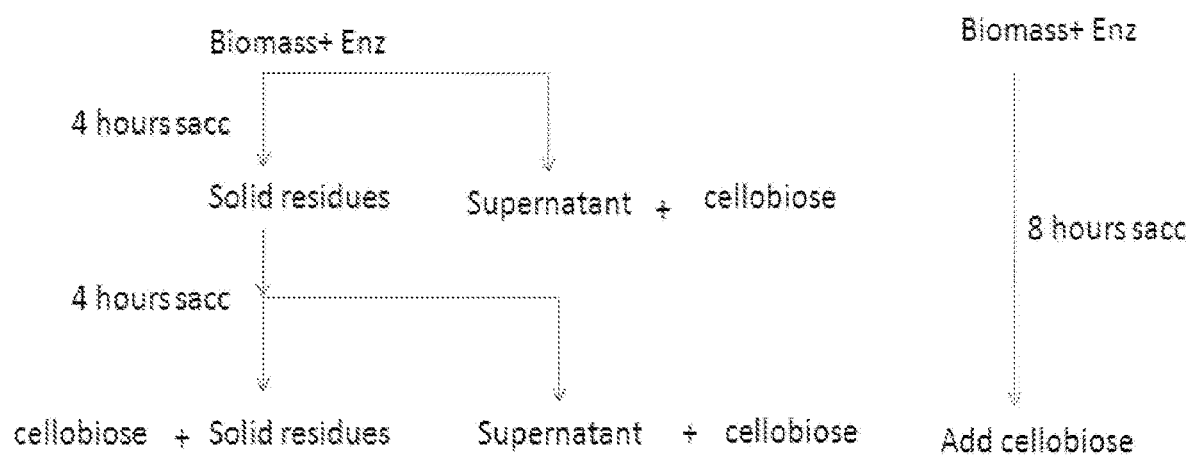
FIG. 20 shows a schematic of biomass saccharified using a cellolosic enzyme cocktail and cellobiose.

The overall schematic of the system for generating sugar from biomass is depicted in FIG. 19. The bagasse biomass was pretreated for 40 minutes at 179° C. The bagasse slurry was transferred into the first of 5 augers, the mix auger, at 12% solids. No liquid recycle occurred into this auger. Accellerase Trio® was added to the bagasse in the mix auger at a dose of 20% enzyme by weight with respect to the glucan in the bagasse. Additionally, polyethylene glycol (PEG) was added to the biomass in the mix auger at a dose of 2% PEG by mass with respect to the solids mass in the solution. The augers were insulated and internal auger temperatures were maintained at 50° C. The solid phase was moved through the mix auger using a screw conveyer and was pumped to the next auger, which was the first of four saccharification augers (see FIG. 19). In the saccharification augers, the auger liquid phase was separated from the auger solids using a mesh screen located at or near the beginning of the auger but after the inlet. The auger solid phase was moved through each saccharification auger using a screw conveyer and was pumped to the next auger.

Solids leaving the end of the fourth saccharification auger were recycled back to the start of the first saccharification auger at the point where the material from the mix auger was added. To aid in the auger liquor removal from the saccharification augers, these augers were operated with a 3° incline from start to end. After passing through the auger screen, the liquid was run through a vibrating screen (Sweco, Florence, KY) with a 25 μm or 43 μm screen. The solids that did not pass through the screen were recycled back into the auger system. The liquid was then sent to a TFF system which consisted of a 9.8 m2 module containing a 150 kDa polyether sulfone (PES) membrane (SmartFlow Technologies, Apex, NC). The retentate from the TFF was periodically recycled back into the saccharification augers while the permeate containing additional sugars was removed from the system.

Activities for endoglucanase (Endo), exocellulase (Exo), and beta-glucosidase (BG) were measured at key points in the continuous auger saccharification process to demonstrate enzyme recycle. Endoglucanase activity was measured using azo-CM-cellulase, exoglucanase using p-nitrophenyl-β-D-lactopyranoside, and β-glucosidase (BG) using p-nitrophenyl-β-D-glucopyranoside assays, respectively. Enzymes adsorbed to biomass solids were first desorbed using a dispersant and the resulting solution diafiltered. Liquid samples were diafiltered as received. Total cellulase activity of the two fractions was calculated based on the volume of these two fractions, respectively.

Sample points included the enzyme addition point (point 1 in FIG. 19), the solid and liquid feeds to the Sweco vibrating screen (point 2 in FIG. 19) and the concentrate and permeate produced by the tangential flow filter (TFF) system (points 3 and 4 in FIG. 19). Activities measurements were combined with the volume of recycled material to calculate the overall recycled activity of each of the above activities. The analysis then was normalized to the initial enzyme concentration to determine the fraction of each enzyme that was returned to the auger system via either the screen recycle stream or the TFF recycle stream.

This analysis calculated the enzyme activity recycled in the higher solids stream from the vibrating screen and from the TFF retentate (Table 2). The feed to the vibrating screen contained 1.20× the overall endoglucanse activity, 0.60× the overall exoglucanase activity, and 0.84× the overall BG activity. The residual activities to the vibrating screen vary greatly between the different enzyme activities because of differences in component enzyme activity loss over time at conditions found in the auger saccharification process. Because the endoglucanse had the least reduction in activity and thus the highest measured relative residual activity in the auger saccharification, it also had the highest relative feed to the vibrating screen. In fact, the endoglucanse that was fed to the vibrating screen was higher than the total endoglucanse fed into the system, a clear indication of the high degree of endoglucanase recycle during the run prior to sampling.

The vibrating screen separates the large solids (roughly larger than 50 μm) from the dissolved solids. The solids fraction has an enzyme activity per gram of material roughly 8 to 12 times higher than the liquid fraction as measured by the above described technique. The vibrating screen is very effective at capturing the solids and enzymes and recycling them back to the saccharification system. In the case of all three enzymes, roughly 70% of the enzymes fed into the vibrating screen were recycled back to the saccharification system.

After the vibrating screen the material containing dissolved solids and non dissolved particles that passed through a 50 μm mesh opening were processed by the TFF. In the TFF, the enzymes and glucan are concentrated while the sugars pass through the membrane. The concentrate from the TFF was recycled back to the saccharification system. This recycle stream contained 0.16× the overall endoglucanse activity, 0.08× the overall exoglucanase activity, and 0.08× the overall BG activity. The overall quantity of enzyme activity units recycled by the TFF system was much lower than the recycle from the vibrating screen because the screen had already removed about ⅔ of the enzyme activity units before it moved on to the TFF system. Additionally, enzyme activity remained in the concentrate tank at the end of the run. Therefore, on a continuous run, this activity would also be recycled back into the saccharification system.

TABLE 2

Relative enzyme activity present in different process streams during saccharification of bagasse using a continuous auger process.

| | Relative Activity | | |
|---|---|---|---|
| | Endo | Exo | BG |
| Feed to System | 1.00 | 1.00 | 1.00 |
| Feed to vibrating screen | 1.20 | 0.60 | 0.84 |
| Recycle from Screen to augers (Solids Phase) | 0.81 | 0.43 | 0.58 |
| Recycle from TFF to augers | 0.16 | 0.08 | 0.08 |
| Concentrate Tank | 0.07 | 0.04 | 0.03 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for generating sugars from biomass, comprising:
   (a) hydrothermally pretreating the biomass at a temperature from about 150° C. to about 210° C. with a high shear/milling mixing device comprising a rotor and a stator, wherein the high shear/milling mixing device has a gap setting between the rotor and stator of between 0.1 and 2.2 millimeters, thereby reducing the size of biomass particles in the biomass, wherein the pretreating results in production of less than about 10% by weight fermentable sugars;
   (b) contacting the biomass with a hydrolytic or saccharification enzyme to hydrolyze components of the biomass to sugars, thereby producing a mixture of solids and a liquid comprising sugars;
   (c) separating the mixture into a liquid stream comprising sugars and furfural, and a solids stream comprising solids and the hydrolytic or saccharification enzyme, wherein the activity of the hydrolytic or saccharification enzyme from step (b) is increased;
   (d) incubating the solids stream under conditions suitable to hydrolyze components of the solids to sugars, thereby producing additional sugars;
   (e) separating the liquid stream produced in (c) into a second liquid stream comprising sugars and a second solid stream comprising solids; and
   (f) incubating the second solid stream under conditions suitable to hydrolyze components of the solids to sugars, thereby producing additional sugars.

2. The method of claim 1, wherein prior to the pretreatment step (a), the biomass is mixed with water to provide a biomass/water mixture.

3. The method of claim 1, wherein the biomass comprises glucan and at least 80% of the glucan in the biomass is hydrolyzed to glucose in about 6 to about 24 hours.

4. The method of claim 1, wherein the biomass is a lignocellulosic biomass.

5. The method of claim 1, wherein the biomass comprises at least about 10% solids w/w prior to the contacting step.

6. The method of claim 1, wherein the biomass is a pretreated biomass.

7. The method of claim 1, wherein the conditions in step (a) produce a biomass particle size wherein at least about 80% of the particles have a particle size of from about 2 to about 200 microns.

8. The method of claim 1, wherein the mixture is separated using a mechanical device, a filter, a membrane, or a tangential flow filtration device.

9. The method of claim 8, wherein the mechanical device is a centrifuge, a press, or a screen.

10. The method of claim 1, wherein the separating step occurs at about 2 to about 4 hours after the contacting step.

11. The method of claim 1, wherein the separating step occurs at about 4 to about 6 hours after the contacting step.

12. The method of claim 3, wherein the separating step occurs when about 30% to about 60% of the glucan is converted.

13. The method of claim 1, wherein the incubating step is from about 8 to about 20 hours.

14. The method of claim 3, wherein the amount of glucan hydrolyzed is at least 10% greater than the amount of glucan hydrolyzed when compared to a method that does not comprise the separating step.

15. The method of claim 1, further comprising contacting the solids from step (c) with additional biomass in a batch, semi-batch, or continuous process.

16. The method of claim 15, wherein the additional biomass comprises additional catalyst.

17. The method of claim 1, wherein the incubating step occurs under conditions of high shear agitation.

18. The method of claim 1, wherein the sugars from the liquid stream in step (b) and/or the additional sugars from step (c) are processed into ethanol, biofuels, biochemicals, or other chemical products.

19. The method of claim 1, wherein the hydrolyzed components from step (d) contain decreased concentrations of furfural compared to biomass from step (b) that is not treated under the conditions as in step (c).

20. The method of claim 16, wherein the additional catalyst comprises additional enzyme and/or a non-enzymatic catalyst.

* * * * *